US012747214B2

(12) United States Patent
Xu

(10) Patent No.: US 12,747,214 B2
(45) Date of Patent: Sep. 29, 2026

(54) IMIDAZOLE-BASED SYNTHETIC LIPIDOIDS FOR IN VIVO mRNA DELIVERY INTO IMMUNE CELLS

(71) Applicant: Trustees of Tufts College, Medford, MA (US)

(72) Inventor: Qiaobing Xu, Lexington, MA (US)

(73) Assignee: Trustees of Tufts College, Medford, MA (US)

( * ) Notice: Subject to any disclaimer, the term of this patent is extended or adjusted under 35 U.S.C. 154(b) by 950 days.

(21) Appl. No.: 17/909,260

(22) PCT Filed: Mar. 2, 2021

(86) PCT No.: PCT/US2021/020450
§ 371 (c)(1),
(2) Date: Sep. 2, 2022

(87) PCT Pub. No.: WO2021/178396
PCT Pub. Date: Sep. 10, 2021

(65) Prior Publication Data

US 2023/0097743 A1 Mar. 30, 2023

Related U.S. Application Data

(60) Provisional application No. 62/983,997, filed on Mar. 2, 2020.

(51) Int. Cl.

| | |
|---|---|
| ***C07D 233/61*** | (2006.01) |
| ***A61K 9/1272*** | (2025.01) |
| ***A61K 31/282*** | (2006.01) |
| ***A61K 31/337*** | (2006.01) |
| ***A61K 31/454*** | (2006.01) |
| ***A61K 31/506*** | (2006.01) |
| ***A61K 31/513*** | (2006.01) |
| ***A61K 31/519*** | (2006.01) |
| ***A61K 31/69*** | (2006.01) |
| ***A61K 31/704*** | (2006.01) |
| ***A61K 31/7048*** | (2006.01) |
| ***A61K 31/7056*** | (2006.01) |
| ***A61K 31/7068*** | (2006.01) |
| ***A61K 38/14*** | (2006.01) |
| ***A61K 47/52*** | (2017.01) |
| ***C12N 15/88*** | (2006.01) |

(52) U.S. Cl.

CPC .......... *C07D 233/61* (2013.01); *A61K 9/1272* (2013.01); *A61K 31/282* (2013.01); *A61K 31/337* (2013.01); *A61K 31/454* (2013.01); *A61K 31/506* (2013.01); *A61K 31/513* (2013.01); *A61K 31/519* (2013.01); *A61K 31/69* (2013.01); *A61K 31/704* (2013.01); *A61K 31/7048* (2013.01); *A61K 31/7056* (2013.01); *A61K 31/7068* (2013.01); *A61K 38/14* (2013.01); *A61K 47/52* (2017.08); *C12N 15/88* (2013.01)

(58) Field of Classification Search

CPC .................................................... C07D 233/61

See application file for complete search history.

(56) References Cited

U.S. PATENT DOCUMENTS

| | | | | |
|---|---|---|---|---|
| 4,097,475 | A * | 6/1978 | James ..................... | C09B 31/02 534/769 |
| 9,512,073 | B2 * | 12/2016 | Dong .................... | C07C 229/36 |
| 2004/0132788 | A1 | 7/2004 | Chabrier De Lassauniere et al. | |
| 2010/0075964 | A1 | 3/2010 | Busch et al. | |
| 2023/0097743 | A1 | 3/2023 | Xu | |

FOREIGN PATENT DOCUMENTS

| | | | |
|---|---|---|---|
| WO | WO-2006/138380 | A2 | 12/2006 |
| WO | WO-2006/138380 | A3 | 7/2008 |
| WO | WO-2010/062322 | A2 | 6/2010 |
| WO | WO-2013/063468 | A1 | 5/2013 |
| WO | WO-2019/152848 | A1 | 8/2019 |
| WO | WO-2021/178396 | A1 | 9/2021 |

OTHER PUBLICATIONS

Ishikawa M et al, J Med Chem. May 13, 2010;53(9):3840-4. doi: 10.1021/jm901890s. PMID: 20384344. (Year: 2010).*
CAS STNext, Abstract for Nguyen et al. PNAS 2012 E797-E803, Registry No. 1416511-22-2, 2012 (Year: 2012).*
Nguyen et al. PNAS 2012 E797-E803 Supporting Information, 2012 (Year: 2012).*
CAS STNext, Abstract for Biomaterials 2018 625-662, Registry No. 2227008-67-3, 2018 (Year: 2018).*
Li et al. Combinatorial library of chalcogen-containing lipidoids for intracellular delivery of genome-editing proteins. Biomaterials. Sep. 2018;178:652-662. doi: 10.1016/j.biomaterials.2018.03.011. Epub Mar. 8, 2018. PMID: 29549971. (Year: 2018).*
Wang et al. ACIE 2014 53 2893-2898 Combinatorially Designed Lipid-like Nanoparticles for Intracellular Delivery of Cytotoxic Protein for Cancer Therapy (Year: 2014).*
Nguyen DN et al. Lipid-derived nanoparticles for immunostimulatory RNA adjuvant delivery. Proc Natl Acad Sci U S A. Apr. 3, 2012; 109(14):E797-803. doi: 10.1073/pnas.1121423109. Epub Mar. 15, 2012. (Year: 2012).*
Carey et al., "Effective 1,5-, 1,6- and 1,7-remote stereocontrol in reactions of alkoxy- and hydroxy-substituted allylstannanes with aldehydes," Organic & Biomolecular Chemistry, 9: 3896-3919 (2011).
International Search Report and Written Opinion for International Application No. PCT/US21/20450 dated Jul. 15, 2021.
Invitation to Pay Additional Fees for International Application No. PCT/US2021/020450 dated May 5, 2021 (Our Reference TUV-14225).

(Continued)

*Primary Examiner* — Bruck Kifle
*Assistant Examiner* — Kevin S Martin
(74) *Attorney, Agent, or Firm* — Foley Hoag LLP; Dana M. Gordon; Alexander J. Chatterley

(57) ABSTRACT

Disclosed are lipid compounds comprising imidazole heads and lipidoid nanoparticles (LNPs) comprising the lipidoid compounds disclosed herein for efficient nucleic acid delivery to T cells.

13 Claims, 15 Drawing Sheets

(56) References Cited

OTHER PUBLICATIONS

PubChem Compound Record for CID 53985319, N-(1H-Imidazol-2-yl)-N-methylhexanamide., U.S. National Library of Medicine, Dec. 4, 2011 (Dec. 4, 2011), pp. 1-8 (https://pubchem.ncbi.nlm.nih.gov/compound/53985319).
PubChem Compound Record for CID 66674076, 'N-(1H-Imidazol-2-yl)-N-methylacetamide', U.S. National Library of Medicine, Nov. 30, 2012 (Nov. 30, 2012), pp. 1-8 (https://pubchem.ncbi.nlm.nih.gov/compound/66674076).
Alabi et al., "Multiparametric approach for the evaluation of lipid nanoparticles for siRNA delivery." Proceedings of the National Academy of Sciences 110(32) (2013): 12881-12886.
Berry et al., "Poly (β-amino ester) s promote cellular uptake of heparin and cancer cell death." Chemistry & Biology 11(4) (2004): 487-498.
Extended European Search Report for EP Application No. 21764086.1 dated Mar. 18, 2024.
Wang et al., "A combinatorial library of unsaturated lipidoids for efficient intracellular gene delivery." ACS synthetic biology 1.9 (2012): 403-407.
Wang et al., "Combinatorially designed lipid?like nanoparticles for intracellular delivery of cytotoxic protein for cancer therapy." Angewandte Chemie International Edition 53.11 (2014): 2893-2898.
Wang et al., "Efficient delivery of genome-editing proteins using bioreducible lipid nanoparticles." Proceedings of the National Academy of Sciences 113.11 (2016): 2868-2873.

* cited by examiner amine head (RNH2)

tail (R' and R")

10 17 63 75

76 77 78 80

81 82 87 90

93 103 113 123

304 306 400

O17O O17S O17Se O12S-S O14S-S O16S-S O18S-S N12S-S N14S-S N16S-S EC12 EC16 EC18

93

93 analogue 9310 9311 9312

9314 9316 9313 9315

9321 9322 9323 9324

9331 9332 9333 9334

9341 9351 9352

Hetero atom

(e.g.) 9322

X = O, S, C, S-S tail name: O17O, O17S, O17C, O18S-S

Tail length n = 6, 5 tail name: O18S-S, O16S-S

First atom in tail

Y = O, N tail name: O16S-S, N16S-S

EC series n = 6, 5 tail name: EC18, EC16

IMIDAZOLE-BASED SYNTHETIC LIPIDOIDS FOR IN VIVO mRNA DELIVERY INTO IMMUNE CELLS

RELATED APPLICATIONS

This application is the § 371 National Stage of PCT/US2021/020450, filed Mar. 2, 2021; which claims the benefit of priority to U.S. Provisional Patent Application Ser. No. 62/983,997, filed Mar. 2, 2020.

GOVERNMENT SUPPORT

This invention was made with government support under grants R01 EB027170-01 and UG3 TR002636-01 awarded by the National Institutes of Health. The government has certain rights in the invention.

BACKGROUND

Engineering T lymphocytes has tremendous potential in advancing therapeutics of cancer, viral infections, inflammation and autoimmunity. For example, chimeric antigen receptor T cells (CARTs) has become one of the FDA approved lymphoma and leukemia therapies in the past few years 1. In current clinical strategies, intracellular delivery of therapeutic molecules into primary T lymphocytes relies on viral delivery system or physical methods such as electroporation. However, it requires ex vivo enrichment of T lymphocytes, resulting in complex procedures and high cost. Therefore, developing in vivo T cell engineering which provides time-effective and low-cost treatments is essential. mRNA is an emerging approach for cell engineering due to its ease of synthesis, rapid and transient protein expression and minimal risk of mutagenesis. Nanomaterials, including polymer and lipid nanoparticles, have been investigated for mRNA delivery into different types of cells. However, delivery of mRNA to T lymphocytes remains a technical challenge due to limited endocytosis and protein translation of T lymphocytes. Therefore, development of better delivery system for enhanced in vivo T cell engineering is desired.

SUMMARY

In certain aspects, disclosed herein are compounds of formula I:

(I)

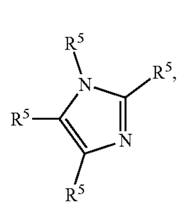

and pharmaceutically acceptable salts thereof, wherein $R^5$ is —W-L-$R^{Lipid}$, hydrogen, halogen, amino, hydroxyl, alkoxy, cyano, nitro, alkyl, alkenyl, alkynyl, cycloalkyl, heterocycloalkyl, aryl, or heteroaryl; wherein one and only one of $R^5$ is —W-L-$R^{Lipid}$.

L is a divalent linker;

W is $NR^{20}$, O, or S;

$R^{Lipid}$ is independently substituted or unsubstituted $C_{1-20}$ alkyl, substituted or unsubstituted $C_{1-20}$ alkenyl, substituted or unsubstituted $C_{1-20}$ alkynyl, substituted or unsubstituted $C_{1-20}$ heteroalkyl, substituted or unsubstituted $C_{1-20}$ heteroalkenyl, or substituted or unsubstituted $C_{1-20}$ heteroalkynyl; and $R^{20}$ is $R^{Lipid}$, H, $C_{1-6}$ alkyl, $C_{1-6}$ alkenyl, or $C_{1-6}$ alkynyl.

In certain embodiments, W is $NR^{20}$ or S. In certain embodiments, W is S. In certain embodiments, W is $NR^{20}$.

In certain embodiments, $R^{20}$ is $R^{Lipid}$.

BRIEF DESCRIPTION OF THE DRAWINGS

FIG. 1A shows the luminescence expression of primary human CD8+ T lymphocytes treated with FLuc mRNA loaded 93-O17S formulated with different ratios of excipients. Only formulated lipidoid showed successful delivery activity. UT: untreated. Data presented as mean±SD, n=3. FIGS. 1B-1C shows the luminescence expression of primary human CD8+ T lymphocytes treated with FLuc mRNA loaded 93-O17S (FIG. 1B) time dependently and (FIG. 1C) dose dependently. UT: untreated. Data presented as mean±SD, n=2.

FIG. 3A is the synthetic route of lipidoids. FIG. 3B shows the chemical structures of amine heads and carbon tails for lipidoids synthesis. FIG. 3C shows the results of rough screening of different lipidoid library in primary human CD8+ T lymphocytes using FLuc mRNA. "F" indicates the lipidoids formulated with cholesterol, DOPE and DSPE-PEG to the weight ratio of 16:4:1:1. "NF" indicates non-formulated lipidoids. LF2000: Lipofectamine 2000. mRNA: mRNA alone without loading to nanoparticles. Data presented as mean±SD, two separate experiments, each in triplicate.

FIG. 4A shows the chemical structures of amine head 93 analogue head. Amine 9310-9315 have different branch on the spacer and different spacer length; Amine 9321-9324 have branch at 2-imidazole; Amine 9331-9334 have branch at 1-imidazole and spacer at 2-imidazole; Amine 9341-9352 have imidazole analogue replaced with imidazole. Structures with red indicate positive effect and blue indicate negative effect on delivery. FIG. 4B shows results of the detailed screening of imidazole analogue heads in primary human CD8+ T lymphocytes using FLuc mRNA. UT: untreated. Data presented as mean±SD, n=3.

FIG. 5A shows the chemical structures of lipidoid with different tail. FIG. 5B shows the results of the detailed screening of lipidoid tails in primary human CD8+ T lymphocytes using FLuc mRNA. Data presented as mean±SD, n=3. *p<0.05. **p<0.005.

FIG. 7A. pKa analysis of lipidoid in detailed amine head 93 analogue library and tail library; FIG. 7B. Hemolysis analysis of lipidoid in detailed amine head 93 analogue library and tail library.

FIGS. 8A-8B. Representative bioluminescence images of (FIG. 8A) whole mouse and (FIG. 8B) organs after injection of FLuc mRNA loaded lipidoids intravenously. FIG. 8C. Tissues and cells were homogenized and lysed to detect luminescence expression from mice injected with FLuc mRNA loaded lipidoids intravenously. Luminescence intensity was normalized to total protein amount. PBS: mice injected with PBS. Data presented as mean±SD, n=3.

FIG. 9A. Representative bioluminescence images of whole mouse with IVIS after injection of FLuc mRNA loaded lipidoids intravenously. FIG. 9B. Representative bioluminescence image of organs with IVIS after injection of FLuc mRNA loaded 9313-O18S—S intravenously. FIG. 9C. In vivo delivery of Cre recombinase mRNA to Ai14 mice intravenously. tdTomato expression in spleen was detected by confocal microscopy 10 days after the injection. T cells were labeled with CD3ε antibody.

FIGS. 10A and 10B. tdTomato expression in spleen was detected by confocal microscopy 10 days after the injection. T cells were labeled with (FIG. 10A) CD3ε antibody and (FIG. 10B) CD8a antibody. FIG. 10C. Flow cytometry analysis of splenocytes 10 days after the injection. tdTomato expression in CD4+ T cells, CD8+ T cells, B cells (CD45R), macrophages (F4/80) and dendritic cells (CD11c) were quantified. Data presented as mean±SD of three mice, each in duplicate. *p<0.05. p<0.005. *p<0.001.

DETAILED DESCRIPTION

Figure 1:
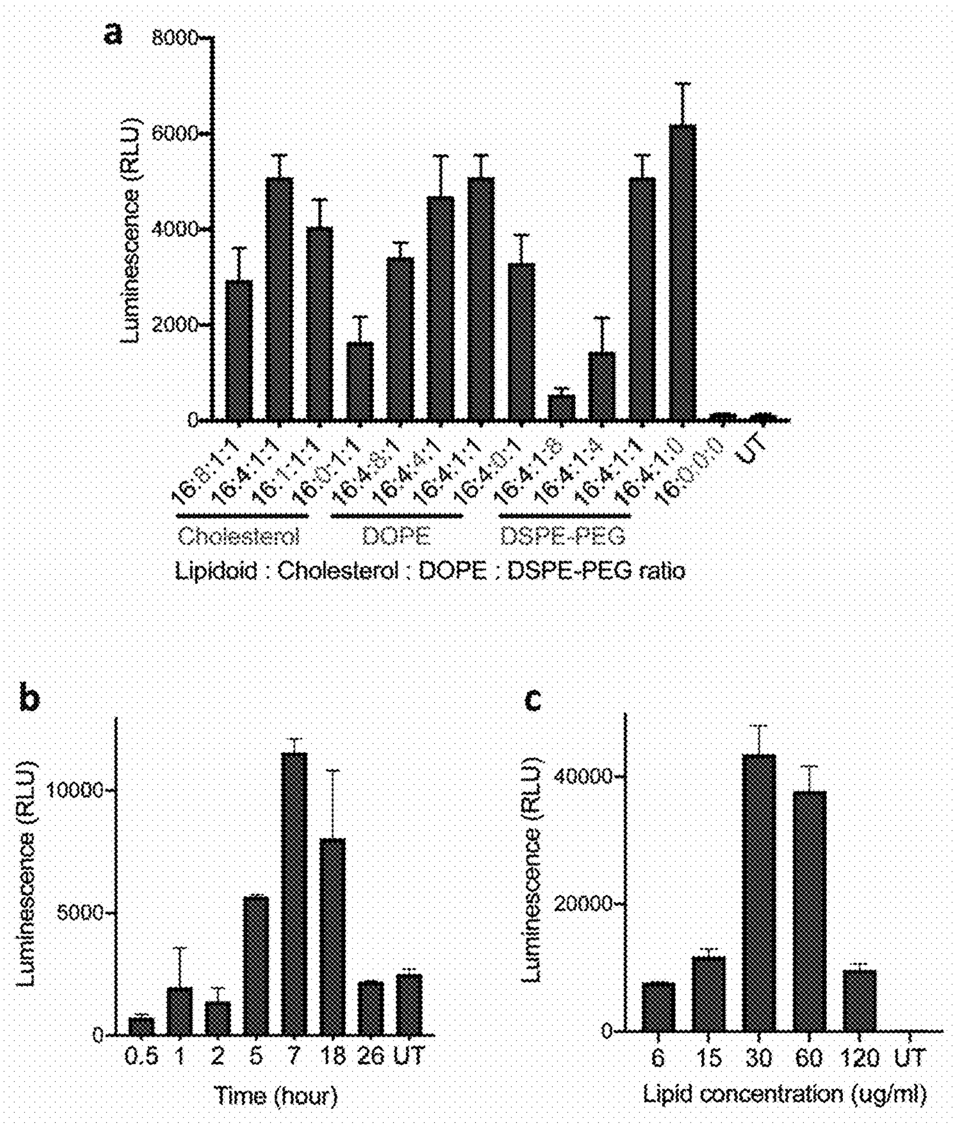
FIGS. 1A-1C show the optimization of lipidoid formulation, delivery time and delivery concentration.
Figure 2:
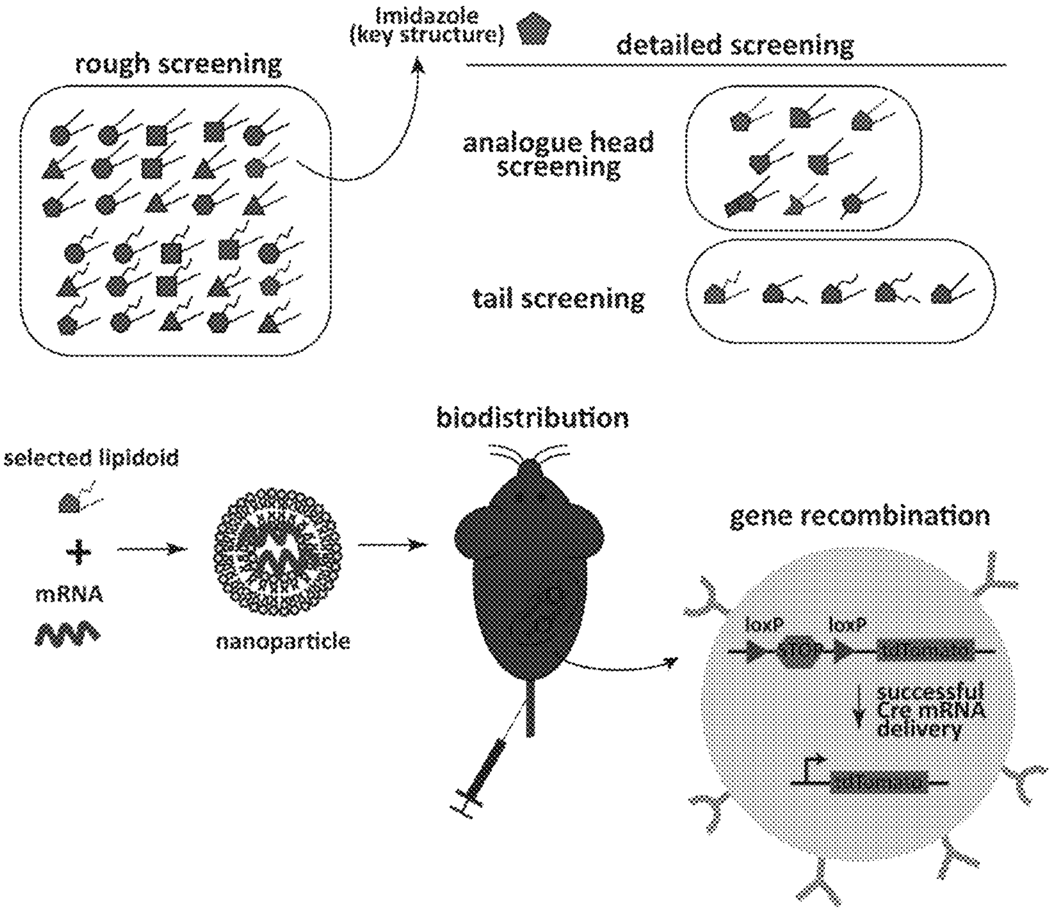
FIG. 2 is a schematic illustration of rough-to-detailed screening. Imidazole containing lipidoids were selected from rough screening. Imidazole and imidazole analogue containing library was constructed for the detailed screening. Lipidoids selected from the screening were used for bioluminescence and gene recombination in vivo.

In certain aspects, disclosed herein are compounds of formula I:

(I)

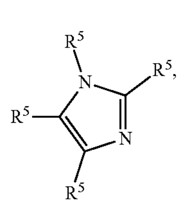

and pharmaceutically acceptable salts thereof, wherein $R^5$ is —W-L-$R^{Lipid}$, hydrogen, halogen, amino, hydroxyl, alkoxy, cyano, nitro, alkyl, alkenyl, alkynyl, cycloalkyl, heterocycloalkyl, aryl, or heteroaryl; wherein one and only one of $R^5$ is —W-L-$R^{Lipid}$.

L is a divalent linker;

W is $NR^{20}$, O, or S;

$R^{Lipid}$ is independently substituted or unsubstituted $C_{1-20}$ alkyl, substituted or unsubstituted $C_{1-20}$ alkenyl, substituted or unsubstituted $C_{1-20}$ alkynyl, substituted or unsubstituted $C_{1-20}$ heteroalkyl, substituted or unsubstituted $C_{1-20}$ heteroalkenyl, or substituted or unsubstituted $C_{1-20}$ heteroalkynyl; and $R^{20}$ is $R^{Lipid}$, H, $C_{1-6}$ alkyl, $C_{1-6}$ alkenyl, or $C_{1-6}$ alkynyl.

In certain embodiments, W is $NR^{20}$ or S. In certain embodiments, W is S. In certain embodiments, W is $NR^{20}$.

In certain embodiments, $R^{20}$ is $R^{Lipid}$.

In certain embodiments, $R^{Lipid}$ is represented by formula II:

(II)

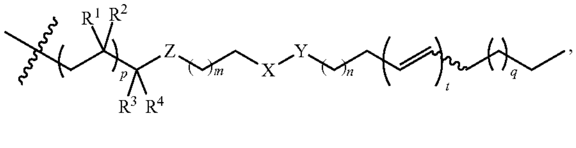

wherein $R^1$ and $R^2$ are independently H, methyl, OH, $NHR^{30}$, or SH;

$R^3$ and $R^4$ are both H; or $R^3$ and $R^4$ are taken together to form an oxo (═O) group;

Z is O, $NR^{30}$, or S;

X and Y are independently $CH_2$, $NR^{30}$, O, S, or Se;

m is an integer selected from 1-3;

n is an integer selected from 1-14;

p is 0 or 1;

q is an integer selected from 1-10;

t is 0 or 1; and $R^{30}$ is H, $C_{1-6}$ alkyl, $C_{1-6}$ alkenyl, or $C_{1-6}$ alkynyl.

In certain embodiments, $R^3$ and $R^4$ are both H. In certain embodiments, $R^3$ and $R^4$ are taken together to form an oxo (═O) group.

In certain embodiments, p is 0. In certain embodiments, p is 1.

In certain embodiments, Z is O, or $NR^{30}$. In certain embodiments, Z is O. In certain embodiments, Z is $NR^{30}$.

In certain embodiments, the compound is a compound of formula III:

(III)

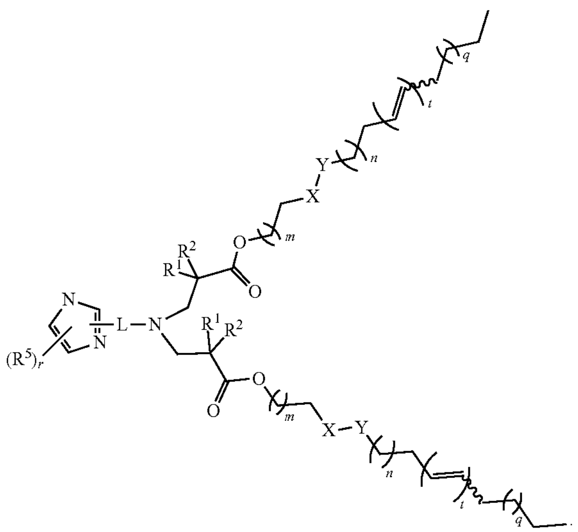

In certain embodiments, $R^1$ and $R^2$ are independently H, methyl, or OH. In certain embodiments, $R^1$ and $R^2$ are both H. In certain embodiments, $R^1$ is H and $R^2$ is methyl. In certain embodiments, $R^1$ is H; and $R^2$ is OH.

In certain embodiments, X and Y are independently $CH_2$ or O. In certain embodiments, X and Y are both $CH_2$. In certain embodiments, X and Y are independently $CH_2$ or O and X and Y are not the same.

In certain embodiments, X and Y are independently $CH_2$ or S. In certain embodiments, X and Y are both S. In certain embodiments, X and Y are independently $CH_2$ or S and X and Y are not the same.

In certain embodiments, m is 1 or 2. In certain embodiments, m is 1.

In certain embodiments, n is an integer selected from 4-12. In certain embodiments, n is an integer selected from 6-10.

In certain embodiments, q is an integer selected from 2-8. In certain embodiments, q is an integer selected from 4-8.

In certain embodiments, t is 0. In certain embodiments, t is 1.

In certain embodiments, L is substituted or unsubstituted $C_{1-6}$ alkylene, substituted or unsubstituted $C_{1-6}$ alkenylene, or substituted or unsubstituted $C_{1-6}$ alkynylene, substituted or unsubstituted $C_{1-6}$ heteroalkylene, substituted or unsubstituted $C_{1-6}$ heteroalkenylene, or substituted or unsubstituted $C_{1-6}$ heteroalkynylene.

In certain embodiments, L is substituted or unsubstituted $C_{1-6}$ alkylene. In certain embodiments, L is unsubstituted $C_{1-6}$ alkylene. In certain embodiments, L is $C_{1-6}$ alkylene substituted by $C_{1-6}$ alkyl.

In certain embodiments, L is selected from the group consisting of

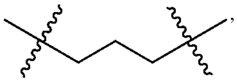,
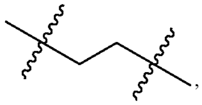,
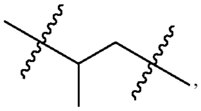,
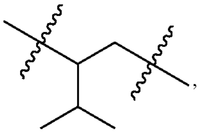,
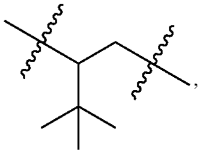,
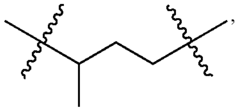,
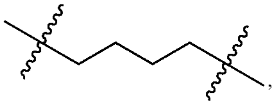, and
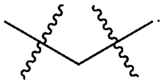.

In certain embodiments, $R^5$ is $C_{1-6}$ alkyl, $C_{2-6}$ alkenyl, $C_{2-6}$ alkynyl. In certain embodiments, $R^5$ is $C_{1-6}$ alkyl.

In certain embodiments,

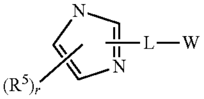

is selected from the group consisting of:

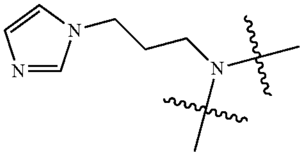,
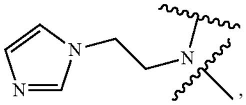,
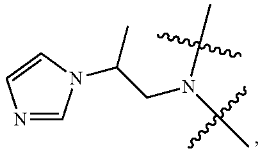,
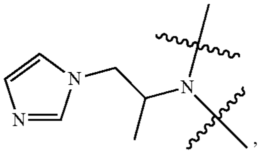,
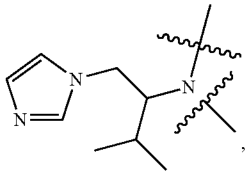,
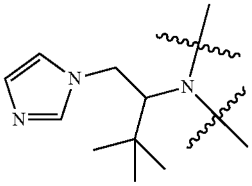,
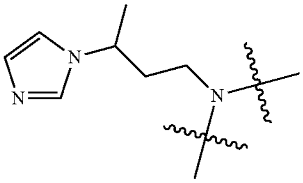,
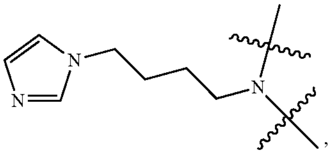,
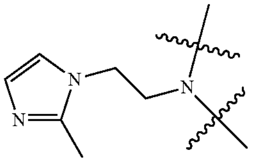,
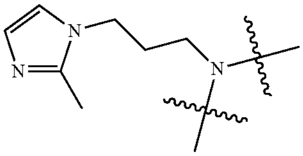,
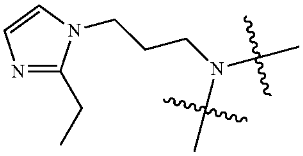, -continued
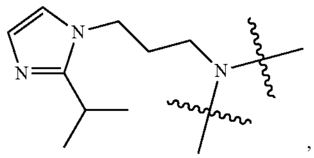
,
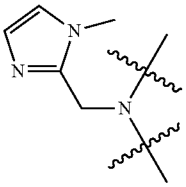
,
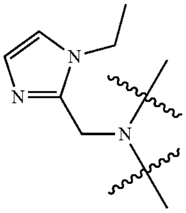
,
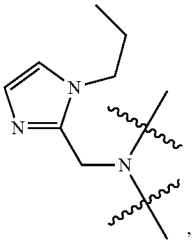
,
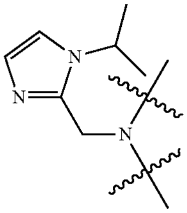
,
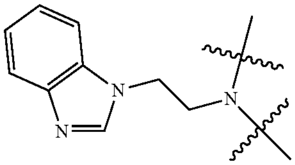
,
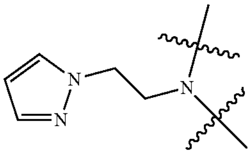
, and
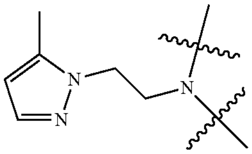
.
In certain embodiments
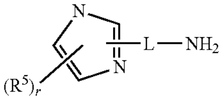
is selected from the group consisting of:
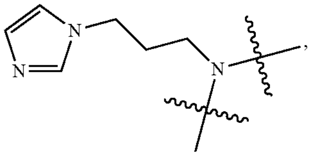
,
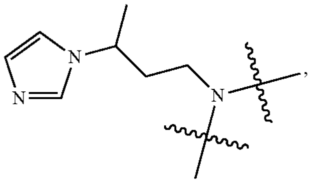
,
-continued
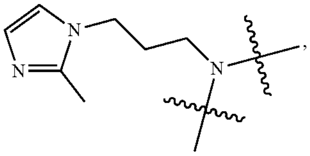
, and
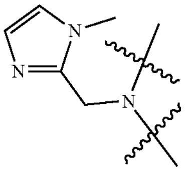
.
In certain embodiments, each instance of $R^{Lipid}$ is independently selected from the group consisting of
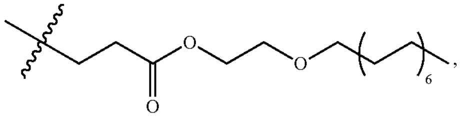
,
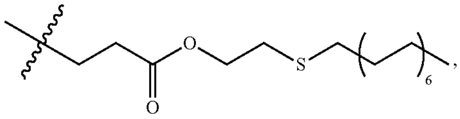
,
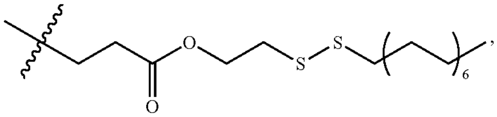
,
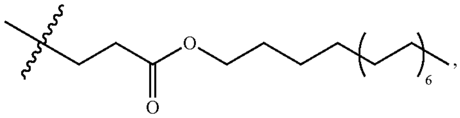
,
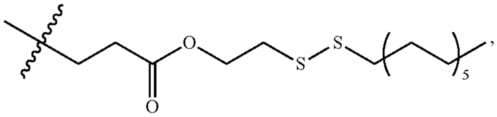
,
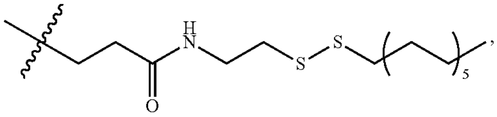
,
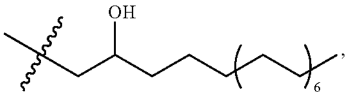
, and
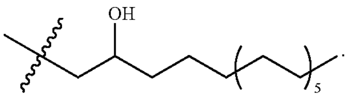
.
In certain embodiments, each instance of $R^{Lipid}$ is independently selected from the group consisting of
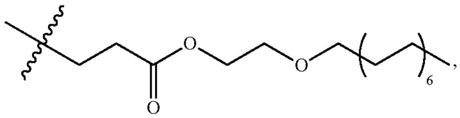
, -continued

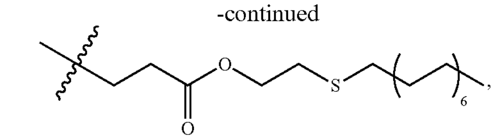,

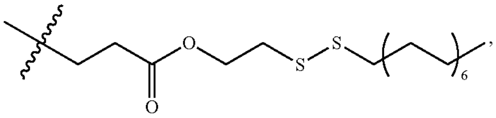, and

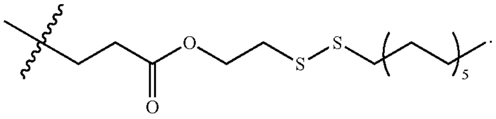.

In certain embodiments,

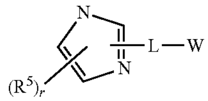

is selected from the group consisting of:

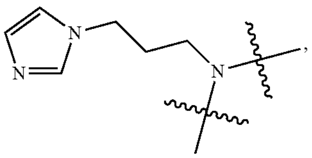,

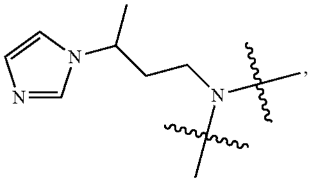,

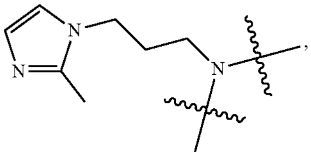, and

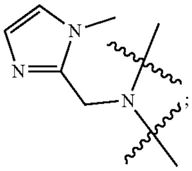;

and each instance of $R^{Lipid}$ is independently selected from the group consisting of

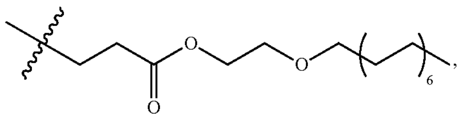,

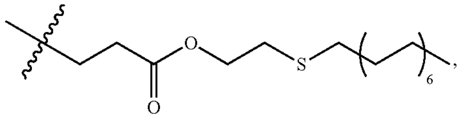,

-continued

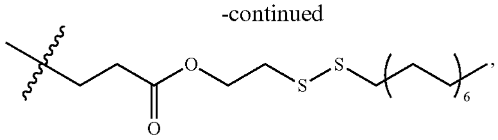, and

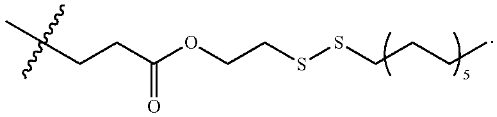.

In another aspect, provided are lipidoid nanoparticles, comprising a compound disclosed herein.

In certain embodiments, the lipidoid nanoparticles further comprise cholesterol.

In certain embodiments, the lipidoid nanoparticles further comprise DOPE or PEG2K-DEPC.

In certain embodiments, the lipidoid nanoparticles further comprise a divalent nickel, wherein the compound chelates with the divalent nickel.

In certain embodiments, the lipidoid nanoparticles further comprise a protein or a nucleic acid.

In certain embodiments, the protein or the nucleic acid is GFP-Cre or CRISPR/Cas9. In certain embodiments, the protein or the nucleic acid is GFP-Cre. In certain embodiments, the protein or the nucleic acid is CRISPR/Cas9.

In certain embodiments, the divalent nickel binds to the protein or the nucleic acid via a non-covalent interaction.

In certain embodiments, the lipidoid nanoparticles further comprise a small molecule.

In certain embodiments, the small molecule is an antifungal agent or a chemotherapeutic agent.

In certain embodiments, the small molecule is selected from the group consisting of Bortezomib, Imatinib, Gefitinib, Erlotinib, Afatinib, Osimertinib, Dacomitinib, Daunorubicin hydrochloride, cytarabine, Fluorouracil, Irinotecan Hydrochloride, Vincristine Sulfate, Methotrexate, Paclitaxel, Vincristine Sulfate, epirubicin, docetaxel, Cyclophosphamide, Carboplatin, Lenalidomide, Ibrutinib, Abiraterone acetate, Enzalutamide, Pemetrexed, Palbociclib, Nilotinib, Everolimus, Ruxolitinib, epirubicin, pirirubicin, idarubicin, valrubicin, amrubicin, Bleomycin, phleomycin, dactinomycin, Mithramycin, streptozotecin, pentostatin, Mitosanes mitomycin C, Enediynes calicheamycin, Glycosides rebeccamycin, Macrolide lactones epotihilones, ixabepilone, pentostatin, Salinosporamide A, Vinblastine, Vincristine, Etoposide, Teniposide, Vinorelbine, Docetaxel, Camptothecin, Hycamtin, Pederin, Theopederins, Annamides, Trabectedin, Aplidine, and Ecteinascidin 743 (ET743).

In certain embodiments, wherein the small molecule is Amphotericin B or Doxorubicin.

In certain embodiments, the lipidoid nanoparticle has a particle size of about 25 nm to about 1000 nm. In certain embodiments, the lipidoid nanoparticle has a particle size of about 50 nm to about 750 nm.

In yet another aspect, provided are pharmaceutical compositions, comprising a lipidoid nanoparticle disclosed herein, and a pharmaceutically acceptable carrier or excipient.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. “Principles of Neural Science”, McGraw-Hill Medical, New York, N.Y. (2000); Motulsky, “Intuitive Biostatistics”, Oxford University Press, Inc. (1995); Lodish et al., “Molecular Cell Biology, 4th ed.”, W. H. Freeman & Co., New York (2000); Griffiths et al., “Introduction to Genetic Analysis, 7th ed.”, W. H. Freeman & Co., N.Y. (1999); and Gilbert et al., “Developmental Biology, 6th ed.”, Sinauer Associates, Inc., Sunderland, MA (2000).

Chemistry terms used herein, unless otherwise defined herein, are used according to conventional usage in the art, as exemplified by “The McGraw-Hill Dictionary of Chemical Terms”, Parker S., Ed., McGraw-Hill, San Francisco, C.A. (1985).

As used herein, the terms “optional” or “optionally” mean that the subsequently described event or circumstance may occur or may not occur, and that the description includes instances where the event or circumstance occurs as well as instances in which it does not. For example, “optionally substituted alkyl” refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term “optionally substituted” refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, “optionally substituted” refers to the replacement of one to four hydrogen radicals in a given structure with the substituents mentioned above. More preferably, one to three hydrogen radicals are replaced by the substituents as mentioned above. It is understood that the substituent can be further substituted.

Articles such as “a,” “an,” and “the” may mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

As used herein, the term “alkyl” refers to saturated aliphatic groups, including but not limited to $C_1$-$C_{10}$ straight-chain alkyl groups or $C_1$-$C_{10}$ branched-chain alkyl groups. Preferably, the “alkyl” group refers to $C_1$-$C_6$ straight-chain alkyl groups or $C_1$-$C_6$ branched-chain alkyl groups. Most preferably, the “alkyl” group refers to $C_1$-$C_4$ straight-chain alkyl groups or $C_1$-$C_4$ branched-chain alkyl groups. Examples of “alkyl” include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The “alkyl” group may be optionally substituted.

The term “acyl” is art-recognized and refers to a group represented by the general formula hydrocarbylC(O)—, preferably alkylC(O)—.

The term “acylamino” is art-recognized and refers to an amino group substituted with an acyl group and may be represented, for example, by the formula hydrocarbylC(O)NH—.

The term “acyloxy” is art-recognized and refers to a group represented by the general formula hydrocarbylC(O)O—, preferably alkylC(O)O—.

The term “alkoxy” refers to an alkyl group having an oxygen attached thereto. Representative alkoxy groups include methoxy, ethoxy, propoxy, tert-butoxy and the like.

The term “alkoxyalkyl” refers to an alkyl group substituted with an alkoxy group and may be represented by the general formula alkyl-O-alkyl.

The term “alkyl” refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term “alkyl” as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term “$C_{x-y}$” or “$C_x$-$C_y$”, when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term “alkylamino”, as used herein, refers to an amino group substituted with at least one alkyl group.

The term “alkylthio”, as used herein, refers to a thiol group substituted with an alkyl group and may be represented by the general formula alkylS—.

The term “amide”, as used herein, refers to a group

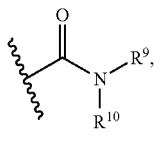

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

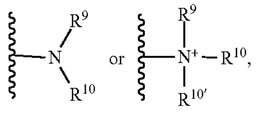

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

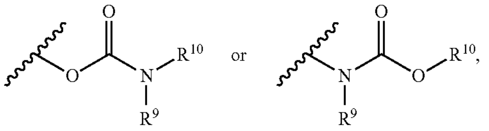

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term “hydroxyalkyl”, as used herein, refers to an alkyl group substituted with a hydroxy group.

The term “lower” when used in conjunction with a chemical moiety, such as, acyl, acyloxy, alkyl, alkenyl, alkynyl, or alkoxy is meant to include groups where there are ten or fewer atoms in the substituent, preferably six or fewer. A “lower alkyl”, for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms “polycyclyl”, “polycycle”, and “polycyclic” refer to two or more rings (e.g., cycloalkyls, cycloalkenyls, cycloalkynyls, aryls, heteroaryls, and/or heterocyclyls) in which two or more atoms are common to two adjoining rings, e.g., the rings are “fused rings”. Each of the rings of the polycycle can be substituted or unsubstituted. In certain embodiments, each ring of the polycycle contains from 3 to 10 atoms in the ring, preferably from 5 to 7.

The term “sulfate” is art-recognized and refers to the group —$OSO_3H$, or a pharmaceutically acceptable salt thereof.

The term “sulfonamide” is art-recognized and refers to the group represented by the general formulae

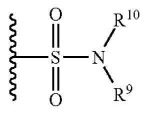

or

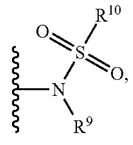

wherein $R^9$ and $R^{10}$ independently represents hydrogen or hydrocarbyl.

The term “sulfoxide” is art-recognized and refers to the group-S(O)—.

The term “sulfonate” is art-recognized and refers to the group $SO_3H$, or a pharmaceutically acceptable salt thereof.

The term “sulfone” is art-recognized and refers to the group —$S(O)_2$—.

The term “substituted” refers to moieties having substituents replacing a hydrogen on one or more carbons of the backbone. It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term “thioalkyl”, as used herein, refers to an alkyl group substituted with a thiol group.

The term “thioester”, as used herein, refers to a group —$C(O)SR^9$ or —$SC(O)R^9$ wherein $R^9$ represents a hydrocarbyl.

The term “thioether”, as used herein, is equivalent to an ether, wherein the oxygen is replaced with a sulfur.

The term “urea” is art-recognized and may be represented by the general formula

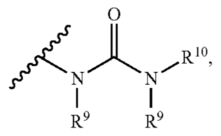

wherein $R^9$ and $R^{10}$ independently represent hydrogen or a hydrocarbyl.

The term “modulate” as used herein includes the inhibition or suppression of a function or activity (such as cell proliferation) as well as the enhancement of a function or activity.

The phrase “pharmaceutically acceptable” is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

“Salt” is used herein to refer to an acid addition salt or a basic addition salt.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like.

The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e. g., Berge, et al., J. Pharm. Sci. 66 (1):1-79 (January 77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural formula indicated herein. Examples of metabolically cleavable groups include —COR, —COOR, —CONRR and —$CH_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkylesters or (alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g., in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g, infant, child, adolescent) or adult subject (e.g., young adult, middle aged adult or senior adult) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention. The "effective amount" can vary depending on the compound, the disease and its severity, and the age, weight, etc., of the subject to be treated. A "therapeutically effective amount" refers to the effective amount for therapeutic treatment. A "prophylactically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention," and refers to a measure or procedure the purpose of which is to prevent, rather than to treat or cure a disease. Non limiting examples of prophylactic measures may include the administration of vaccines; the administration of low molecular weight heparin to hospital patients at risk for thrombosis due, for example, to immobilization, and the administration of an anti-malarial agent such as chloroquine, in advance of a visit to a geographical region where malaria is endemic or the risk of contracting malaria is high.

"Treating" or "treatment" or "therapeutic treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^{2}H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be "$^{2}H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radio-active isotopes tritium, i.e., $^{3}H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the acid- and nitro-forms of phenylnitromethane, that are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 95% by weight R-compound and at most about 5% by weight S-compound, at least about 99% by weight R-compound and at most about 1% by weight S-compound, or at least about 99.9% by weight R-compound and at most about 0.1% by weight S-compound. In certain embodiments, the weights are based upon total weight of compound.

As used herein and unless otherwise indicated, the term "enantiomerically pure S-compound" or "S-compound" refers to at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

EXAMPLES

In order that the invention described herein may be more fully understood, the following examples are set forth. The examples described in this application are offered to illustrate the compounds, compositions, materials, device, and methods provided herein and are not to be construed in any way as limiting their scope.

Materials and Methods

Lipidoid synthesis. Chemicals for lipidoid synthesis were purchased from Sigma-Aldrich and used as received. Aliphatic amine heads and either acrylate tails (O17O, O17S, O17Se, O18S—S, O16S—S, and N16S—S) or epoxide tails (EC18 and EC16) were mixed at 1 to 2.4 molar ratio in Teflon-lined glass screw-top vials at 70° C. for 48 h. The crude products were purified using a Teledyne Isco Chromatography system.

Nanoparticle formulation. Lipidoids, cholesterol, DOPE, and DSPE-PEG were all dissolved in ethanol solution prior to nanoparticle fabrication. For the lipidoid formulation, 16:4:1:1 (Lipidoid:cholesterol:DOPE:DSPE-PEG) w/w ratio was chosen (FIG. 1A). The ethanol solution was added into triple volume of 25 mM sodium acetate buffer (pH 5.2) drop by drop. Formulated nanoparticles were dialyzed in 3.5K MWCO Slide-A-Lyzer dialysis device (Thermo Fisher) for at least 2 h.

Human primary CD8+ T cells isolation. Human peripheral blood mononuclear cells (PBMCs) were purchased from Research Blood Components, LLC. Lymphocytes were isolated by density gradient centrifugation with Lympholyte-H (Cedarlane) and washed with PBS. Red blood cells were lysed using RBC Lysis Buffer (Multi-species) (eBioscience) and washed with PBS. CD8+ T cells were isolated using the CD8+ T cells isolation kit, Human (Miltenyi Biotec) according to the manufacturer's protocol. Purified CD8+ T cells were characterized by flow cytometry with CD3+ antibody.

In vitro luciferase assay for lipidoids screening. Human primary CD8+ T cells were seeded at 25,000 cells per well in 250 μL of serum-free RPMI medium containing 10 ng/mL Recombinant Human IL-2 (BD Biosciences), ImmunoCult Human CD3/CD28 T cell Activator (STEMCELL Technologies), and 100 U/mL Pen-Strep (Gibco) in 48-well plates. FLuc mRNA was delivered into T cells immediately after seeding. For each well, 0.5 μg CleanCap FLuc mRNA (TriLink Biotechnologies) and 5 μg lipidoids were mixed in 50 μL of 25 mM sodium acetate buffer (pH 5.2) and incubated at room temperature for 15 min for encapsulation. Then, mRNA/lipidoid complex was added into cell culture medium at a final concentration of 1.7 μg/mL and 17 μg/mL, respectively. T cells were incubated at 37° C. for 6 h, then lysed to measure luciferase expression using Firefly Luciferase Assay Kit 2.0 (Biotium) and SYNERGY H1 microplate reader (BioTek). Graph represents the average luminescence of experiments in triplicate with error bar expressed as ±SD. The best delivery time and lipidoid concentration was found to be ~6 h and 30 μg/mL, respectively (FIGS. 1B-1C).

In vivo FLuc mRNA delivery and bioluminescence. Lipidoid/mRNA complexes were prepared as described above. 15 μg CleanCap FLuc mRNA (5 moU) (TriLink Biotechnologies) and 150 μg lipidoids were used per mouse in a total volume of 150 μL PBS. Lipidoid/mRNA complexes were injected into BALB/c mice intravenously. After 6 h of injection, 3 mg D-luciferin was injected intraperitoneally and bioluminescence was measured using an IVIS Spectrum CT Biophotonic Imager (PerkinElmer). After the bioimaging, mice were sacrificed and the luminescence from each organ was also measured using the IVIS. Then, FLuc mRNA delivery efficacy into T cells were quantified by luciferase assay. Single-cell suspensions from spleen were collected by passing the splenocytes through 70-μm cell strainers, followed by red blood cell lysis using RBC Lysis Buffer (Multi-species) (eBioscience). Cells were washed once with PBS and CD8+ T cells were collected using CD8a MicroBeads, mouse (Miltenyi Biotec) according to the manufacturer's protocol. Splenocytes and other organs were lysed using Firefly Luciferase Lysis Buffer (Biotium) and luminescence intensity was measured using Firefly Luciferase Assay Kit 2.0 (Biotium) and SYNERGY H1 microplate reader (BioTek). Total protein amount was quantified using Pierce BCA Protein Assay Kit (Thermo Scientific). Luciferase intensity was normalized to total protein amount in the cells or tissues.

In vivo Cre mRNA delivery and confocal microscopy. Lipidoid/mRNA complexes were prepared as described above. 15 μg CleanCap Cre mRNA (5 moU) (TriLink Biotechnologies) and 150 g lipidoids were used per mouse in a total volume of 150 μL PBS. Lipidoid/mRNA complexes were injected into Ai14 mice intravenously every 5 days for twice. After 10 days of first injection, mice were sacrificed and the spleen was collected. For the confocal microscopy imaging, spleen was frozen sectioned into 15 μm in depth. Slices were washed with PBS and fixed with acetone, followed by staining with fluorescent antibodies for CD3ε (APC), CD8a (APC), or F480 (APC). Fluorescent signal from tdTomato and antibodies was observed using SP8 confocal microscope (Leica). For flow cytometry analysis, single-cell suspensions were collected from spleen by passing the splenocytes through 100-μm cell strainers, followed by red blood cell lysis using RBC Lysis Buffer (Multi-species) (eBioscience). Cells were washed once with PBS and stained with fluorescent antibodies for CD4 (APC) and CD8a (APC) in Flow Cytometry Staining Buffer (eBioscience). Fluorescent signal was measured using LSR-II flow cytometer (BD Biosciences).

Results and Discussion

Figure 3A:
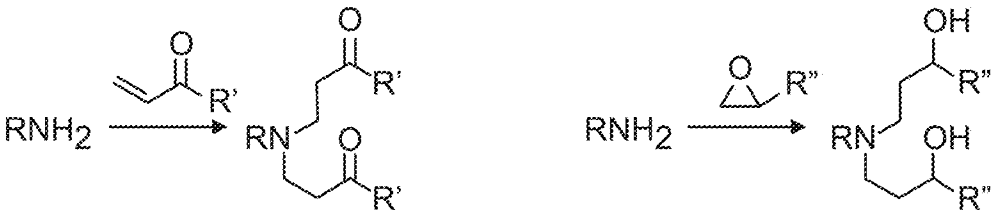
FIGS. 3A-3C show the rough screening of lipidoids for mRNA delivery to primary T lymphocytes in vitro.
Figure 3B:
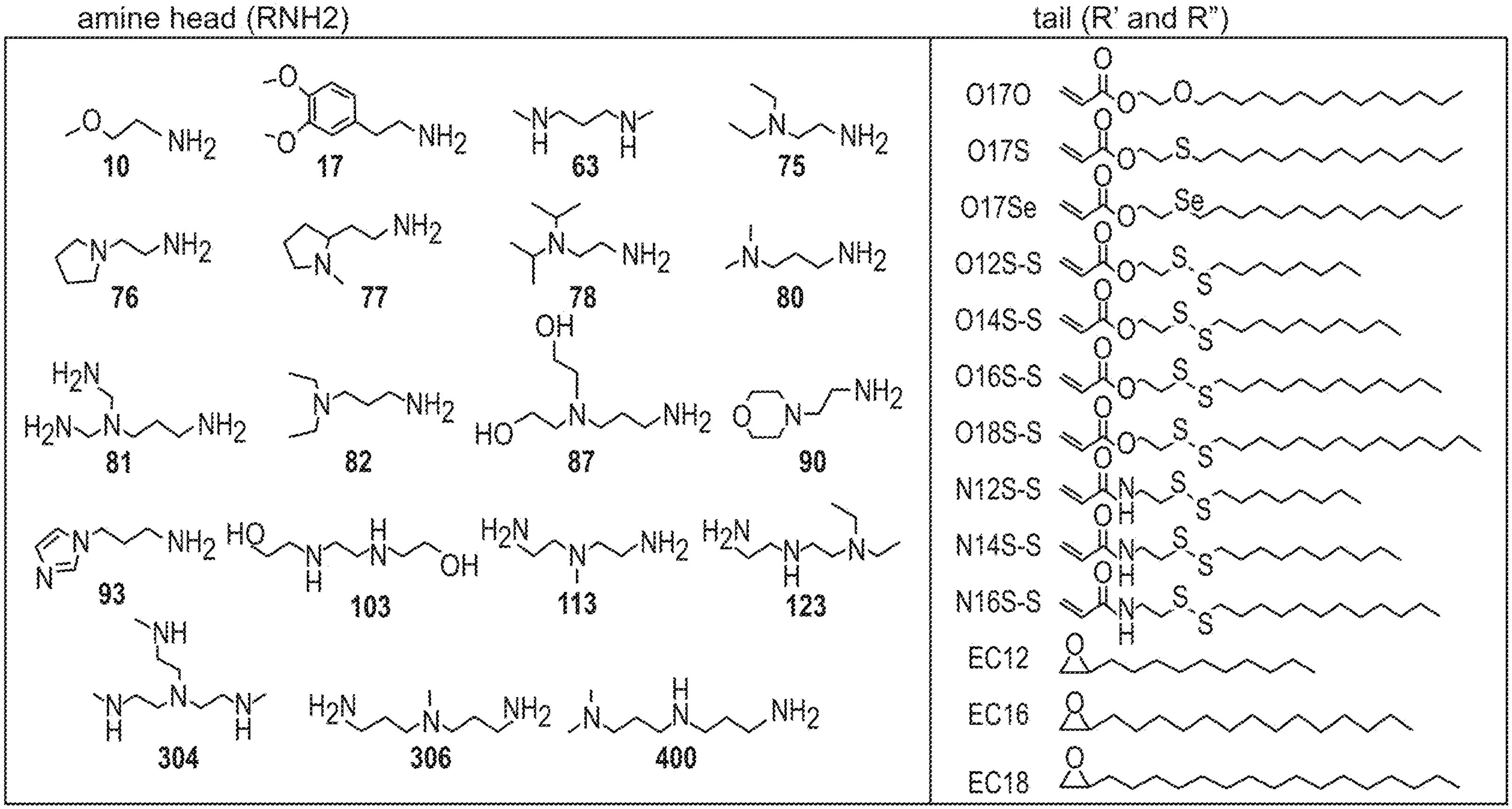

Rough Screening of Lipidoids for mRNA Delivery into Human Primary CD8+ T Cells Cationic lipid-like materials (lipidoid) are synthesized in a combinatorial manner of hydrophilic amine head and hydrophobic carbon tail through Michael addition reaction (FIGS. 3A and 3B).

Figure 3C:
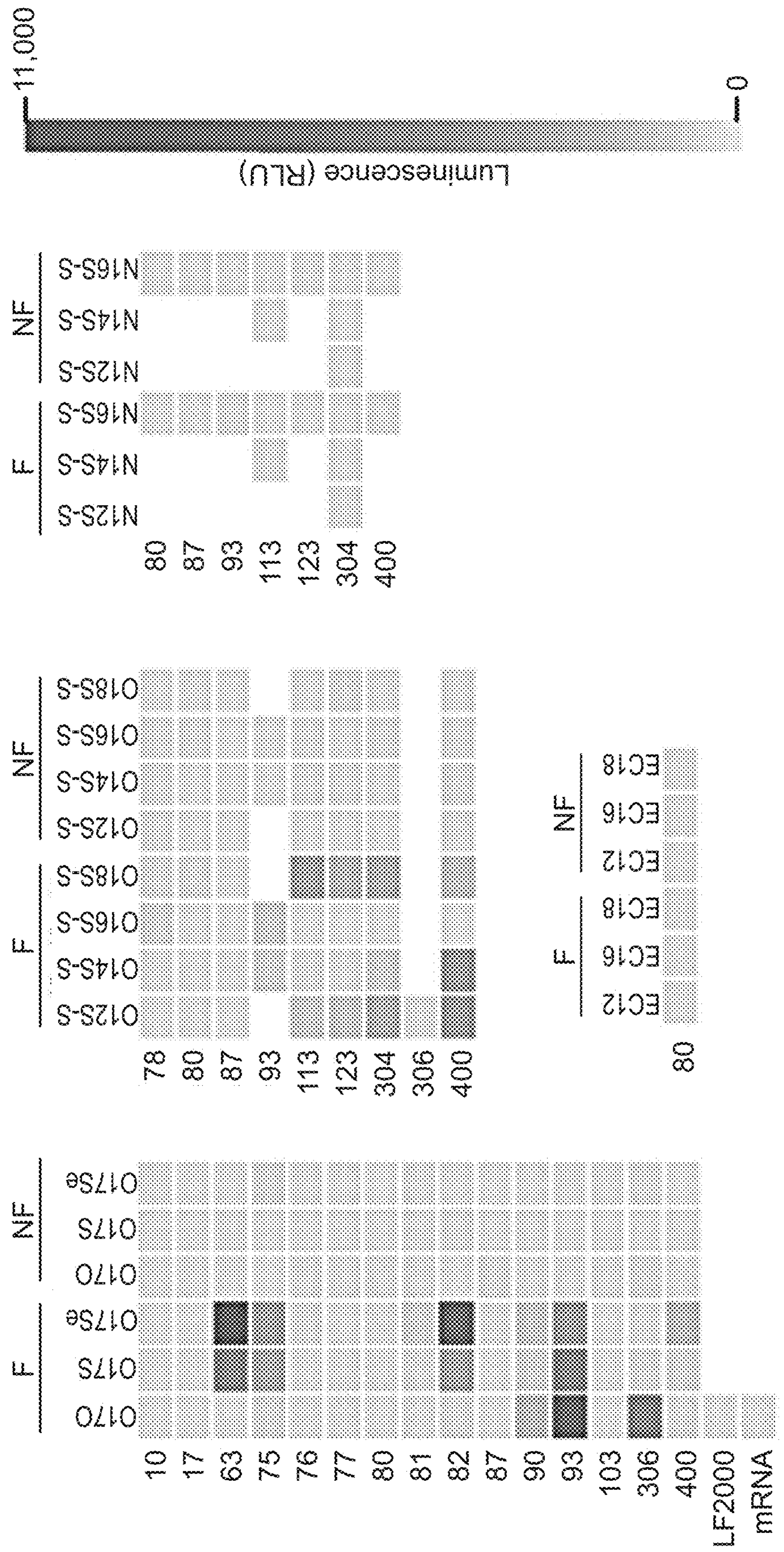

Lipidoids that showed relatively good efficacy for nucleic acid and protein delivery were selected, and a rough screening was conducted for luciferase mRNA delivery to primary T lymphocytes in vitro (FIG. 3C). Lipidoids were named using a naming convention in the form of R-OnX, R-NnX or R-ECn. In all cases, "R" indicates the amine number as shown in FIG. 3B (left column), "n" indicates the number of the carbon in hydrophobic tail before atom substitution, "X" indicates the heteroatom content in tail (0, S, Se, or disulfide), "EC" indicates lipidoids tail was synthesized from epoxide. For the first-step rough screening, both non-formulated and formulated lipidoids with three excipients— i.e., cholesterol, 1,2-dioleoyl-sn-glycero-3-phosphoethanolamine (DOPE) and 1,2-distearoyl-sn-glycero-3-phosphoethanolamine-[poly(ethylene glycol)-2000] (DSPE-PEG) were tested. It was found that none of the lipidoid selected showed effective delivery to T lymphocytes when used alone, but several lipidoids showed effective delivery when formulated with excipients described above (FIG. 3C). Among the various libraries, the library with chalcogen (O, S, Se)-containing tail showed the most effective delivery (FIG. 3C). Interestingly, lipidoids with amine head 93 (1-(3-Aminopropyl)imidazole) constantly showed the effective delivery in all tail variants (93-O17O, 93-O17S and 93-O17Se) (FIG. 3C). Treatment with mRNA alone showed no luminescence expression, indicating that the mRNA itself cannot enter cells without effective lipidoids. Moreover, even the most commonly used commercialized lipid reagent, Lipofectamine 2000 (LF2000), showed no transfection effect at all, revealing the great challenge in T cell transfection by non-viral particles. According to the results from the rough screening, it was found that the lipidoids with an imidazole group (in amine head 93) have great potential in T lymphocyte transfection.

Figure 4A:
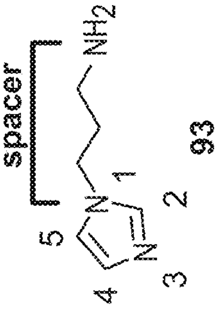
FIGS. 4A-4B show detailed screening of imidazole and imidazole analogue head-containing lipidoids.
Figure 4A:
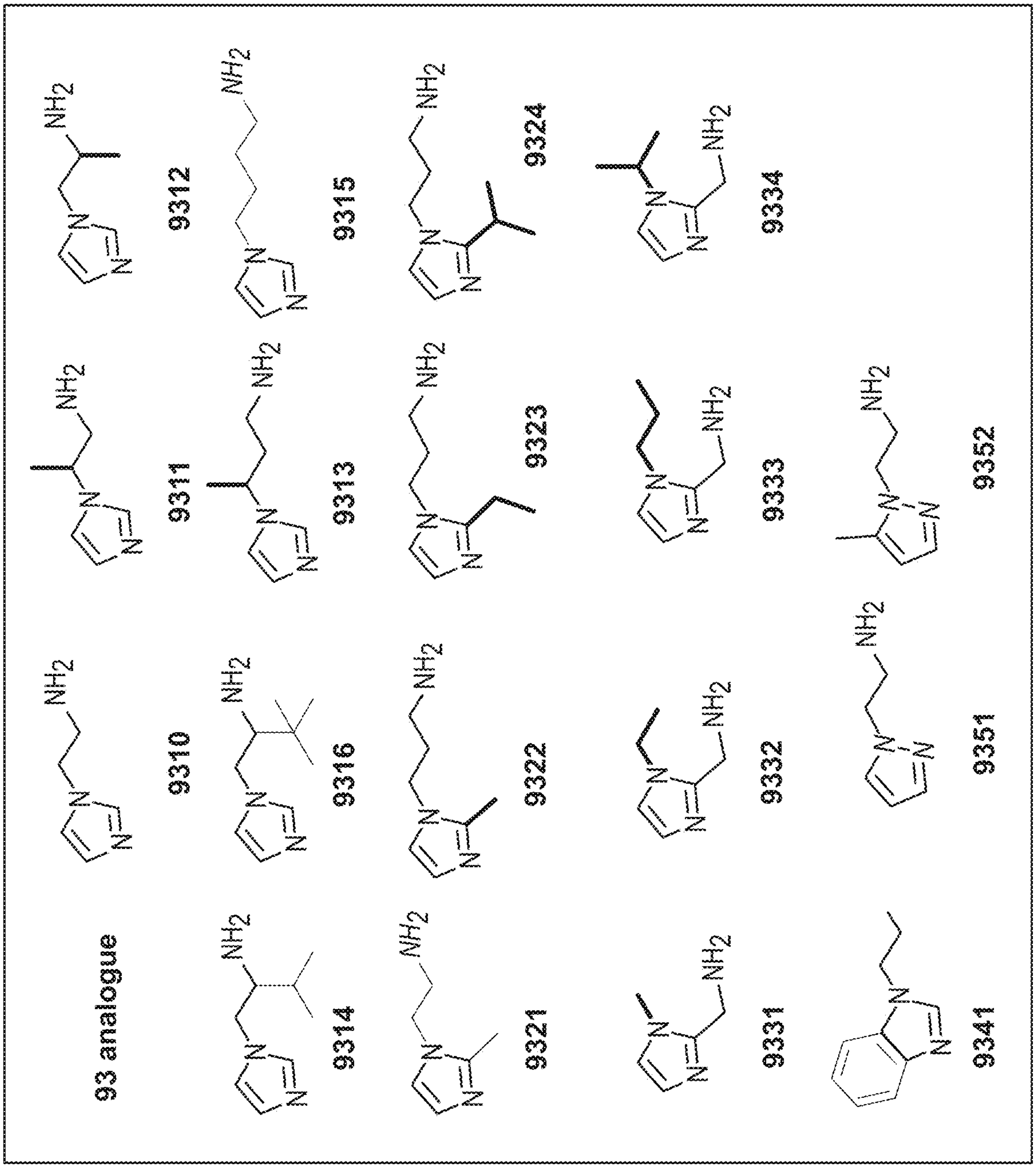

Synthesis and Detailed Screening of Lipidoids Containing Imidazole and Imidazole Analogues Based on the results of the rough screening, it was determined that the imidazole to be the key structure of the lipidoids for mRNA delivery to primary T lymphocytes. New lipidoids containing imidazole or imidazole analogues, shown in FIG. 4A, were subsequently synthesized.

The imidazole or imidazole analogues-containing amine heads were classified into four groups: i) The carbon spacer between the imidazole and amine group was modified with some carbon branch and different length (R: 9310-9315). ii) The different structures of carbon branch were added to 2-imidazole position (R: 9321-9324). iii) The carbon spacer at 1-imidazole position were moved to 2-imidazole position and replaced with the carbon chains with various length and branch (R: 9331-9334). iv) The imidazole ring was replaced with some similar structures (R: 9341-9352). Three aliphatic tail variations (O17O, O17S and O16S—S) were used in constructing the new library through Michael addition reaction.

Figure 4B:
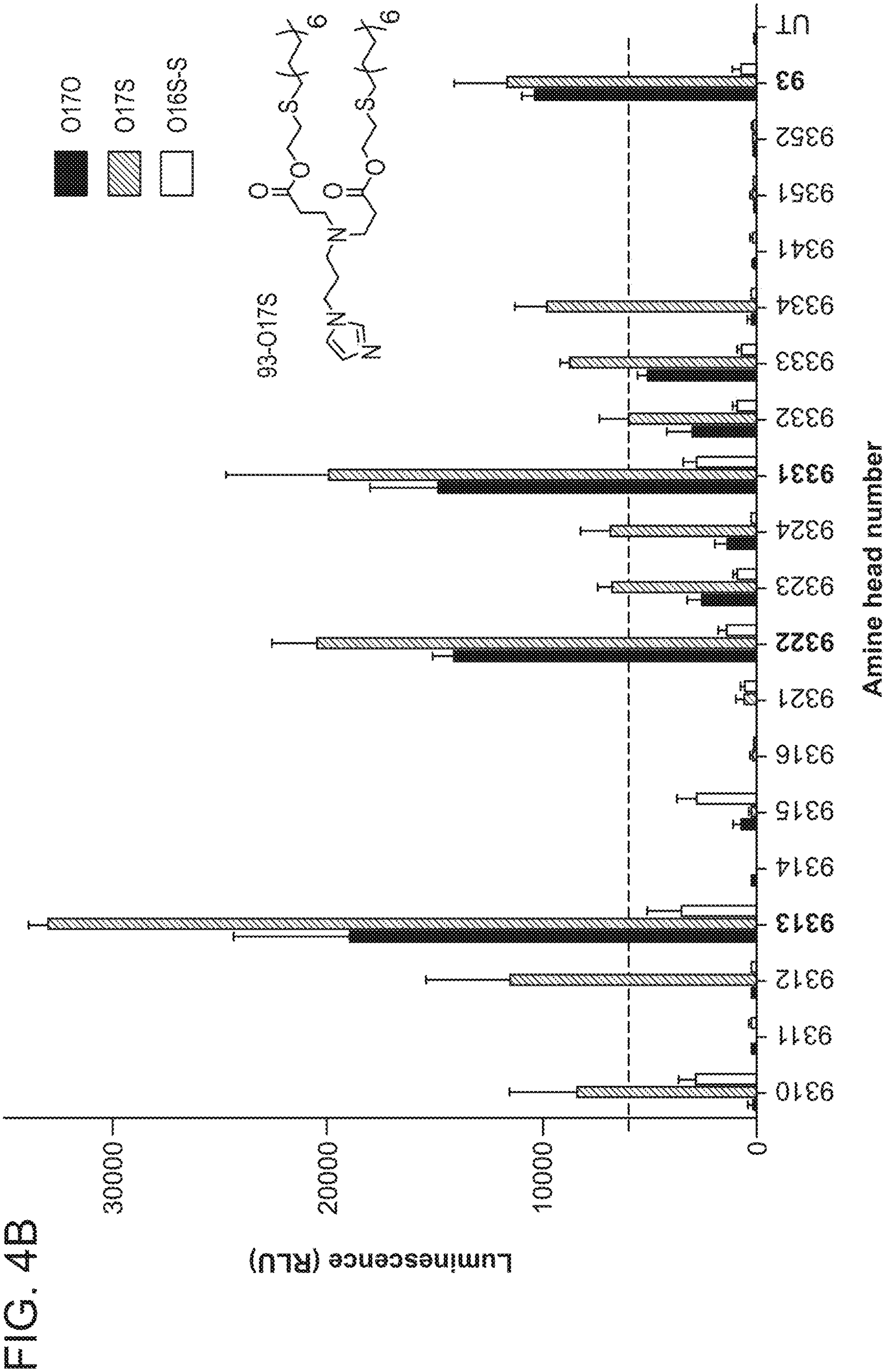

A detailed screening of this new library for luciferase mRNA delivery to primary T lymphocytes in vitro was performed, as shown in FIG. 3*b*, and the correlation between amine head structure and delivery efficacy was investigated. Generally, amine head 9313, 9322, 9331, as well as 93 constantly showed high luminescence expression in lipidoid library. Moreover, there were some trends found in the correlation between chemical structures of amine heads and delivery efficacy. First, when considering the linker branching structure, we found that linkers with a single branch (e.g., 9312 and 9313) showed better efficacy than either the straight-chain linker (e.g., 93, 9310 and 9315) or complex branched linker (e.g., 9314 and 9316). Linker length also appeared to dramatically influence delivery efficacy: the 4-carbon 9315 was not as effective as the 3-carbon 93. Similarly, the 9311 head, which is structurally similar to 9313 but only one carbon shorter, showed no delivery effect at all, while 9313 was extremely effective. Second, it was found that branching at the 2-imidazole position does not affect the delivery potency (e.g., 9322, 9323 and 9324). Third, we noted that within the group with the linker at the 2-imidazole position (e.g., 9331, 9332, 9333 and 9334), all amine heads had some positive signal, indicating that linker position can be ortho-substituted and the branch on imidazole itself does not affect the delivery effect. Last, the amine heads with the imidazole ring analogues (e.g., 9341, 9351, 9352) did not demonstrate any delivery efficacy at all, which proved the imidazole ring is a key structure in T cell delivery of mRNA. In addition to the amine head structure, carbon tail structure also affected the delivery efficacy. Among the effective amine heads (i.e., 9313, 9322, 9331 and 93), lipidoids with O170 and O17S tails tail showed more than 5 fold and 6 fold higher delivery efficacy than lipidoids with O16S—S tail, respectively (FIG. 4B). From these results, it was found that lipidoids synthesized from amine head 9313, 9322, 9331 and 9332 are effective for mRNA delivery to T lymphocytes, and used these amine heads for carbon tail screening.

Detailed Screening of Carbon Tail Structure and Delivery Efficacy

Figure 5A:
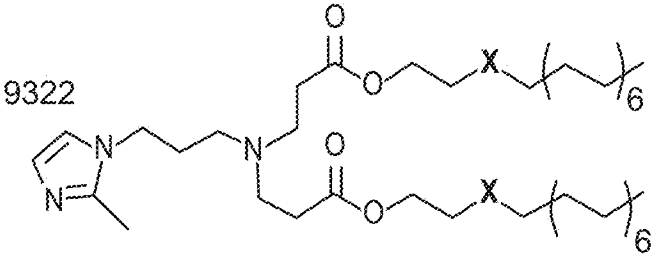
FIGS. 5A-5B shows detailed screening of lipidoid tails.
Figure 5A:
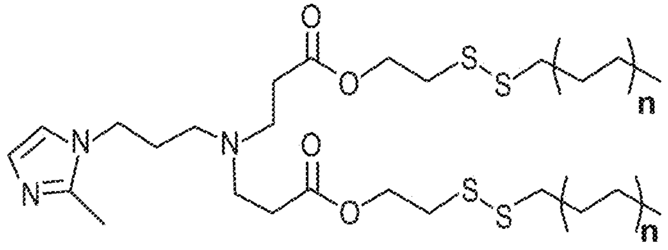
Figure 5A:
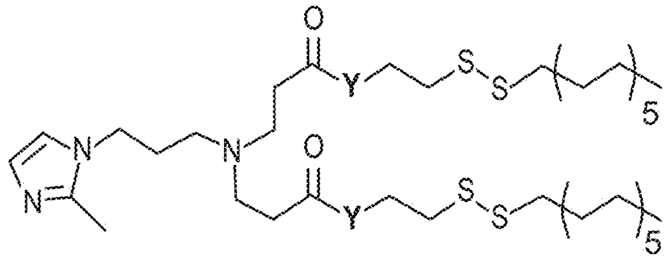
Figure 5A:
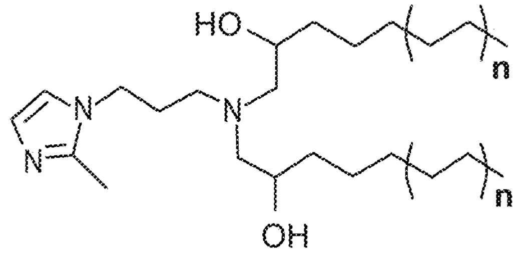
Figure 5B:
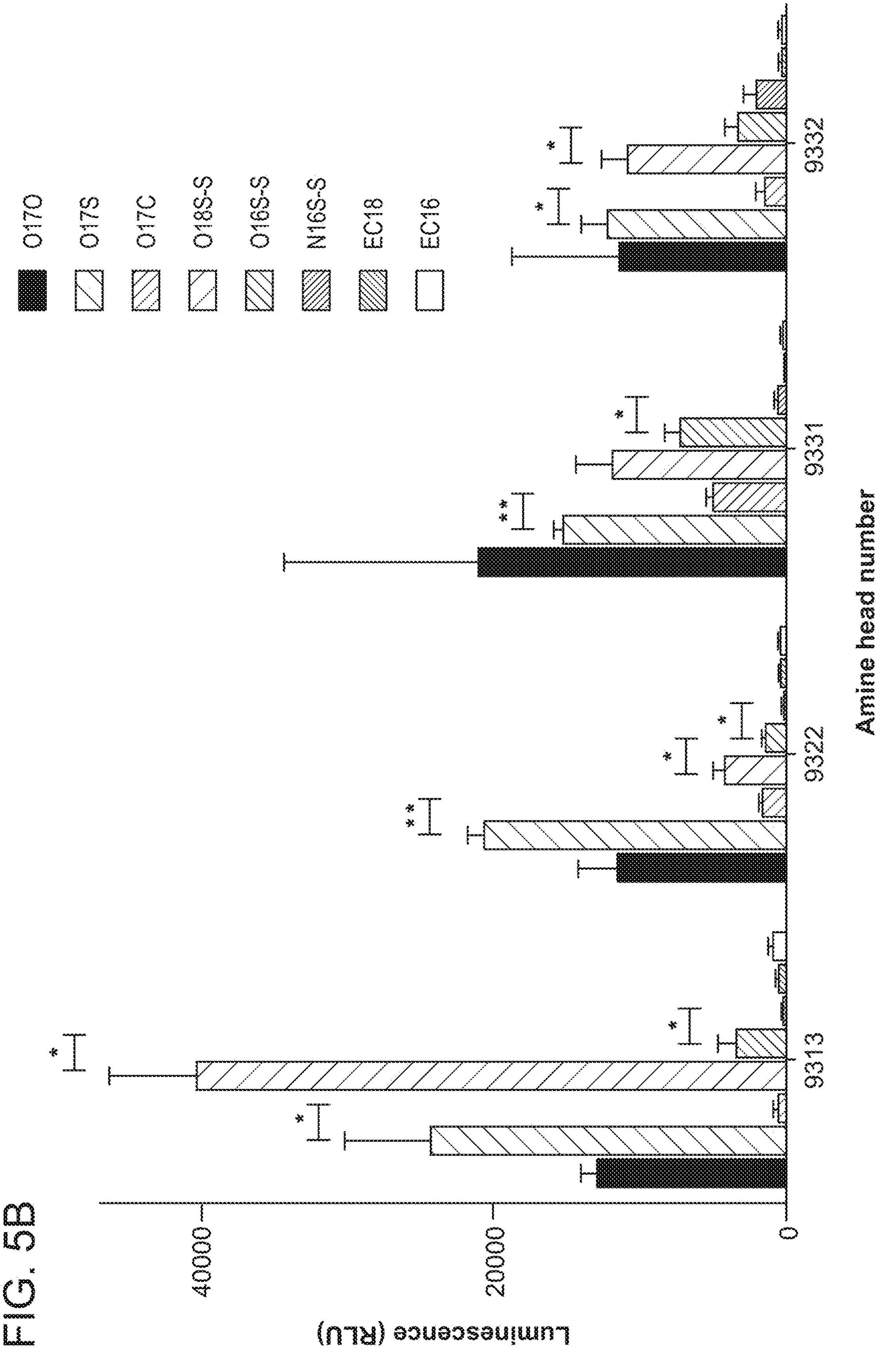

As shown in FIG. 4B, the tails of lipidoids were the other important factor in the delivery efficacy. In order to further study the influence of tail structures on T cell transfection, the detailed lipidoid library with 8 different carbon tails (FIG. 5A) using amine head 9313, 9322, 9331 and 9332 were synthesized, which had high transfection efficacy in previous screening.

Figure 6:
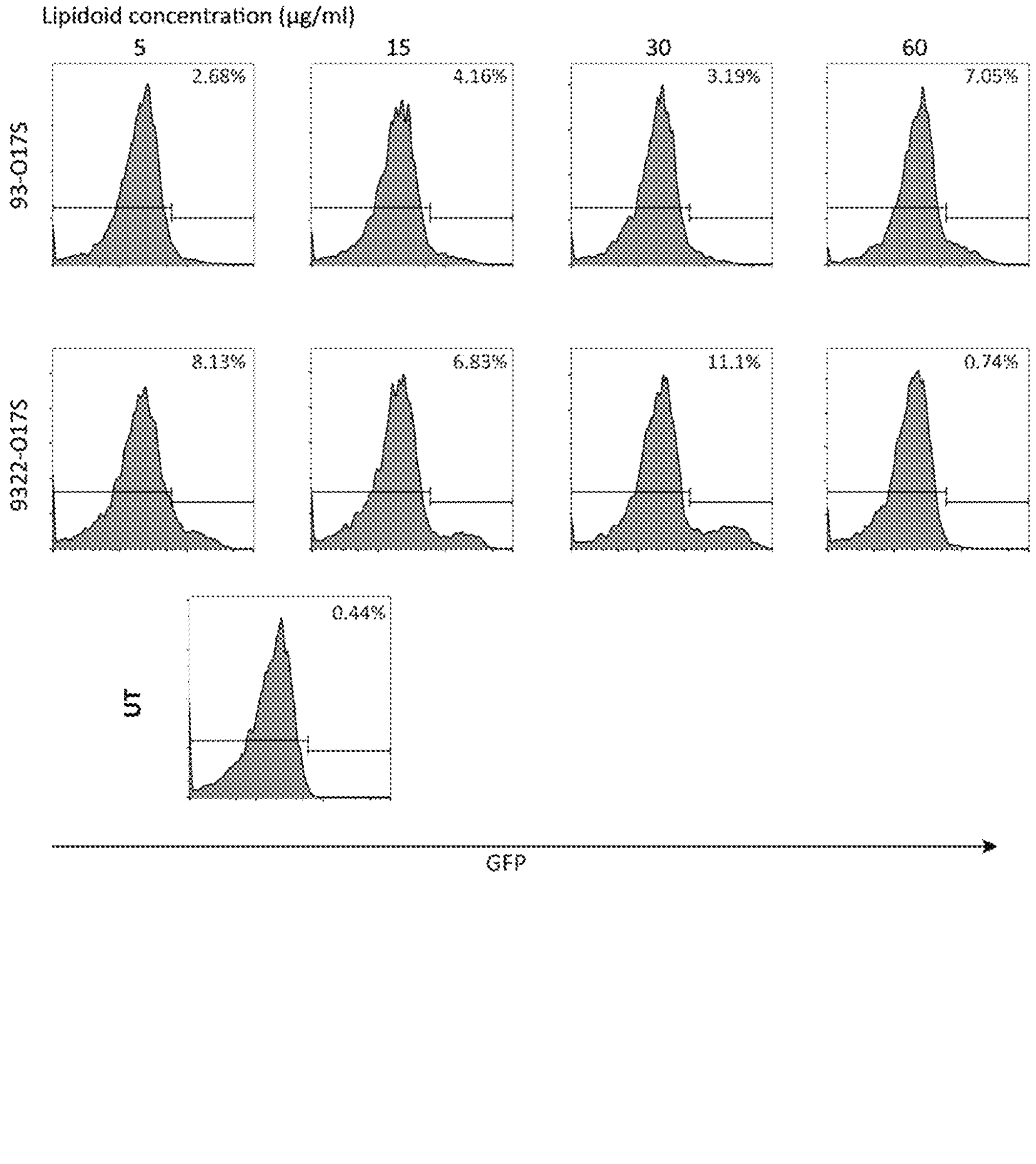
FIG. 6 are graphs that shows the flow cytometry histogram of primary human CD8+ T lymphocytes after treated with EGFP mRNA loaded 93-O17S or 9322-O17S with different concentration. UT: untreated.

As shown in FIG. 4B, lipidoids with O17O, O17S and O18S—S tail consistently worked more efficiently than other tails. Interestingly, for all lipidoids using the O17C tail, in which the entire tail is composed of carbon without any heteroatom, delivery efficacy was significantly reduced. In addition, the length of the carbon chain also affects delivery efficacy. Tail length of 18 carbons, with two of them substituted to S—S (O18S—S), worked significantly more effectively than tail length of 16 (O16S—S). Furthermore, tail with ester bond (O16S—S) worked significantly better than tail with amide bond (N16S—S). Tails made from epoxide (ECn series) did not show effective delivery. In order to elucidate the positive percentage of successfully transfected T cells, EGFP mRNA with 93-O17S and 9322-O17S was delivered into CD8+ T cells in vitro, and quantified GFP expression with flow cytometry. Delivery efficacy into CD8+ T cells reached 7.1% with 93-O17S and 11.1% with 9322-O17S (FIG. 6).

The possible mechanism of the structure-related difference of mRNA delivery to T cells might be related with the various behaviors of LNPs, such as apparent pKa values and membrane disruption abilities. In this study, to further elucidate possible mechanism of the different delivery effect among these lipidoids, the apparent pKa value and phospholipids bilayer membrane disruption ability were further analyzed. There was no big difference in the pKa between effective and ineffective lipidoids, indicating the pKa might not be the main factor determining the delivery efficacy (FIG. 7A).

Figure 7:
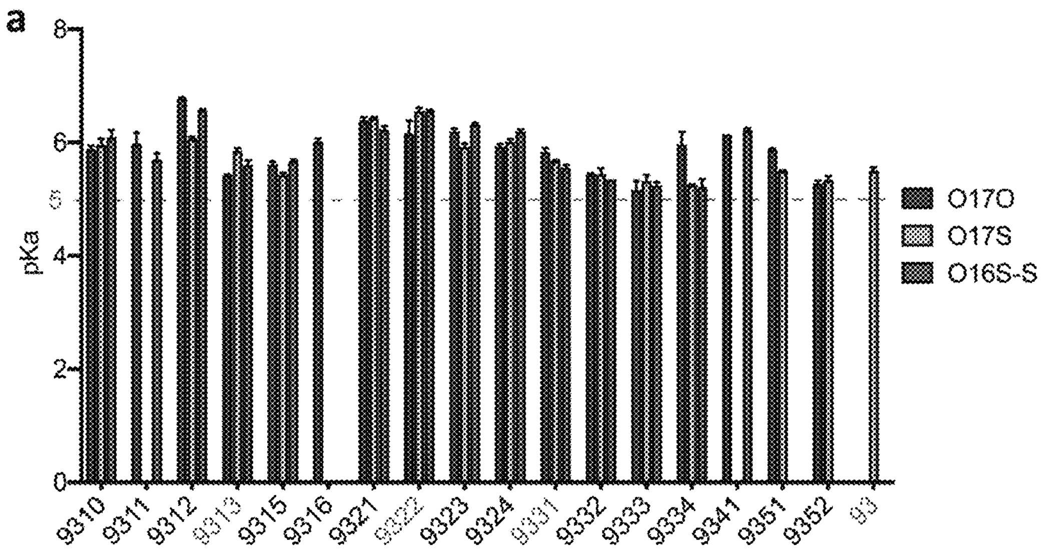
FIGS. 7A-7B are bar graphs of the analysis of pKa and hemolysis of lipidoid nanoparticles.
Figure 7:
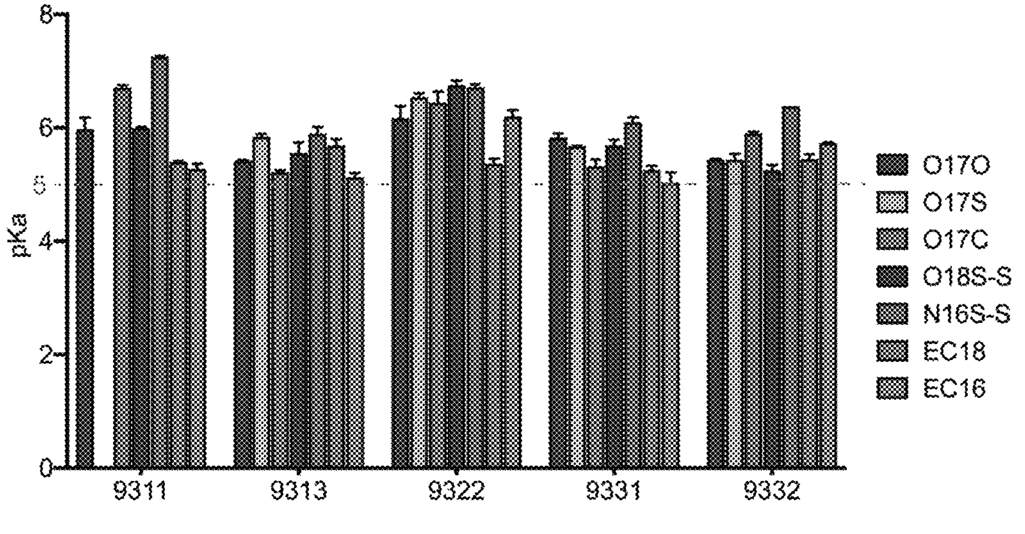
Figure 7:
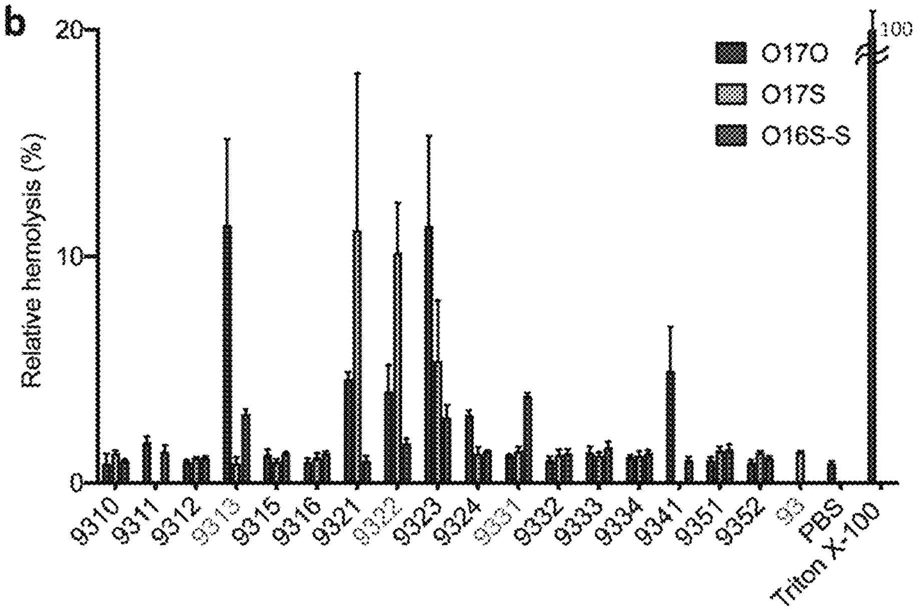
Figure 7:
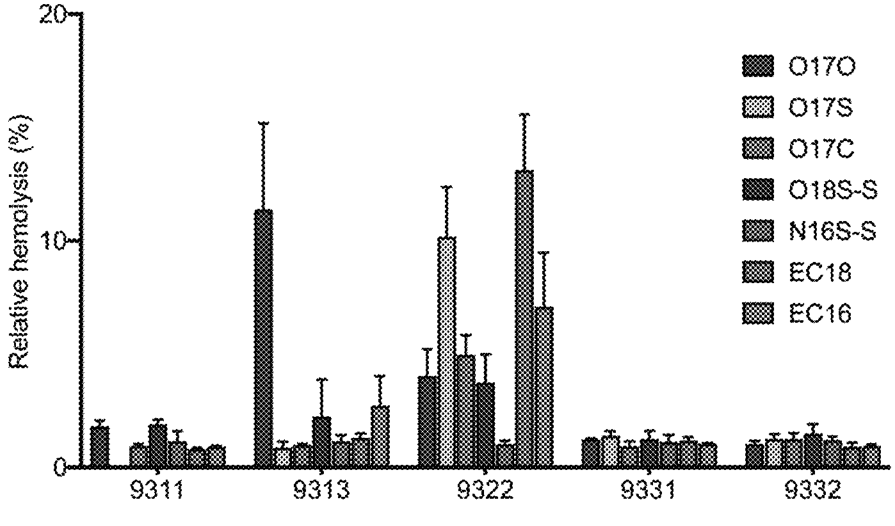

However, as shown in FIG. 7B, most of the successful lipidoids showed higher membrane disruption ability than the unsuccessful ones, especially in these lipidoids with heads in group ii).

In Vivo mRNA Delivery and Biodistribution of Nanoparticles.

Figure 8:
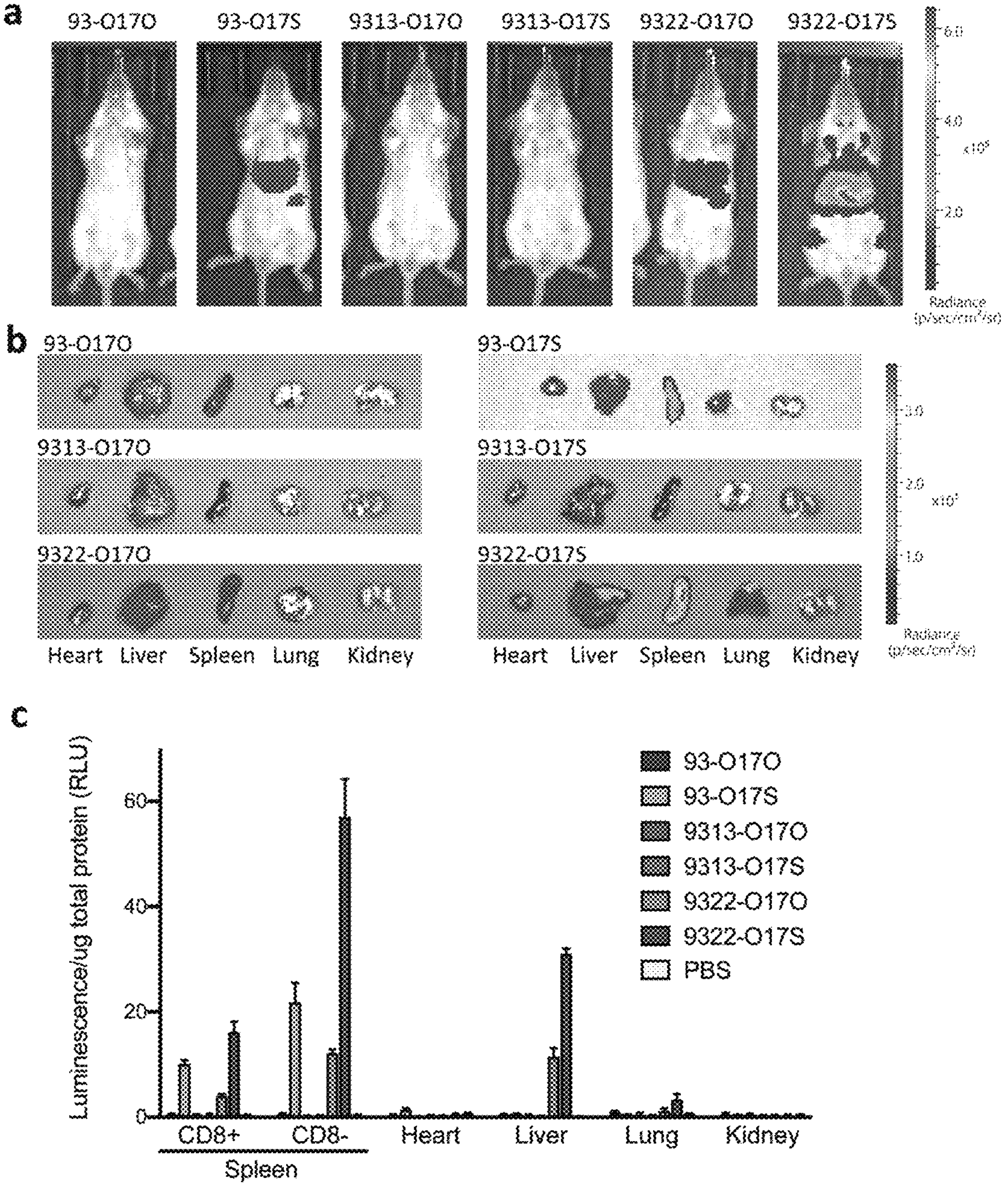
FIGS. 8A-8C are bioluminescence images with IVIS using selected lipidoids.

Even though the in vitro screening proved that the lipidoids found from the structure-based screening can efficiently deliver mRNA into primary T cells, the in vivo delivery effect would be more important for in situ programming of T cells in human body. Moreover, owing to the complex in vivo conditions, the delivery effect in the body mostly may not be consistent with in vitro results. To investigate whether the lipidoids identified by in vitro screening also work in vivo, the effect of lipidoid delivery was also evaluated by intravenous injection of FLuc mRNA and lipidoid complex into BALB/c mouse. 6 h after the injection, bioluminescence was detected in the live mouse, and subsequently the mouse was sacrificed, and bioluminescence specifically from the heart, liver, spleen, lung and kidney was observed. All bioluminescence imaging was performed using an In Vivo Imaging System (IVIS). Amine head 93 and 9322 with O170 and O17S tails showed strong and specific luminescence expression in spleen (FIGS. 8A and 8B).

In the mice delivered with 9322-O17S, the luminescence intensity in spleen was 1.6 folds higher than that in liver. On the other hand, amine head 9313, 9331, and 9332 with O17O, O17S, or O18S—S tails showed no signal in any organs (FIGS. 8A-8C and FIGS. 9A-9B).

Mice were sacrificed and splenocytes were collected to purify CD8+ T cells with magnetic beads. Luminescence expression from either splenocytes or each organ was quantified. Although there was also luminescence signal from liver and other types of cells in spleen, we confirmed the effective delivery into CD8+ T cells using 93-O17S, 9322-O170 and 9322-O17S (FIG. 8C). The luminescence intensity also corresponded to the IVIS results (FIGS. 8B and 8C).

Figure 9:
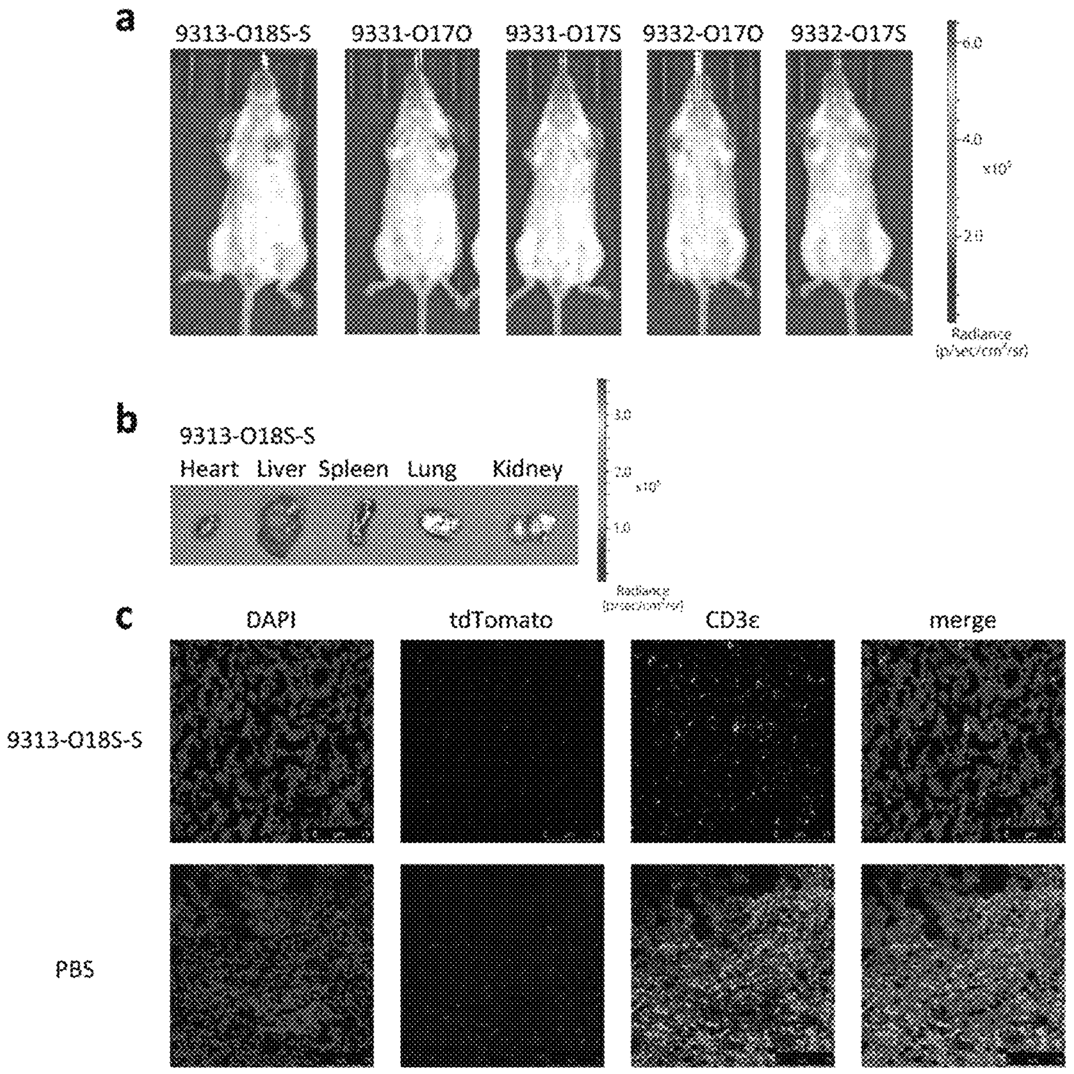
FIGS. 9A-9C are bioluminescence images with IVIS using ineffective lipidoids.

Lipidiods Enhanced Cre Recombinase-Mediated Gene Recombination of Spleen T Cells In Vivo In vivo delivery of gene editing molecules including mRNA, plasmid and RNP into T cells has great potential for application in T cell engineering. The potency of lipidoids for in vivo gene recombination by intravenously delivering Cre recombinase mRNA and lipidoids complex into Ai14 mice (The Jackson Laboratory) was demonstrated. The Ai14 mouse has a genetically integrated STOP codon flanked by IoxP sites located just upstream of a red fluorescent protein (tdTomato) gene 22. The STOP codon can be removed via the activity of Cre protein, which excises the DNA found between the IoxP sites. Therefore, red fluorescence signal is mediated by the successful transfection of Cre mRNA, followed by expression of Cre protein. Cre mRNA/lipidoid complex was injected twice, every 5 days, followed by the analysis of mouse spleen with confocal microscopy. Strong tdTomato expression in spleen was observed from the mouse injected with either 93-O17S or 9322-O17S (FIGS. 10A and 10B), whereas no tdTomato signal was observed from the mouse injected with 9313-O18S—S or PBS alone (FIG. 9C).

Spleen tissue was labeled with either CD3ε or F4/80 antibody to analyze the localization of tdTomato signal with T lymphocytes or macrophages, respectively. In addition, CD8a antibody was used to specifically label CD8+ T lymphocytes. Yellow signal in the fluorescent image indicates the colocalization of the red tdTomato signal and green-tagged cell-type antibodies (indicated by the white arrows) (FIGS. 10A-10B and FIGS. 8A-8C).

Figure 10:
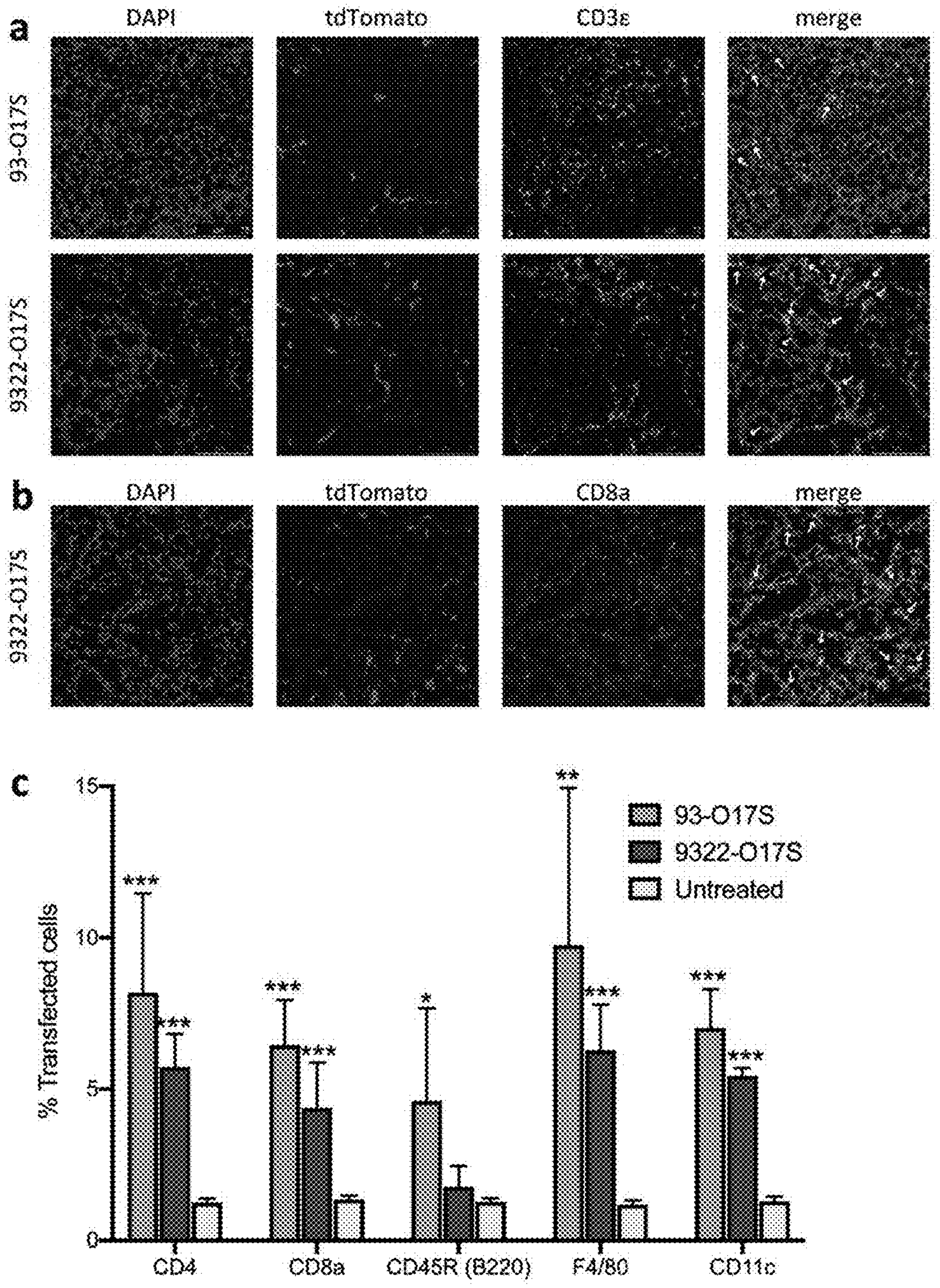
FIGS. 10A-10C show In vivo delivery of Cre recombinase mRNA to Ai14 mice intravenously.
Figure 11:
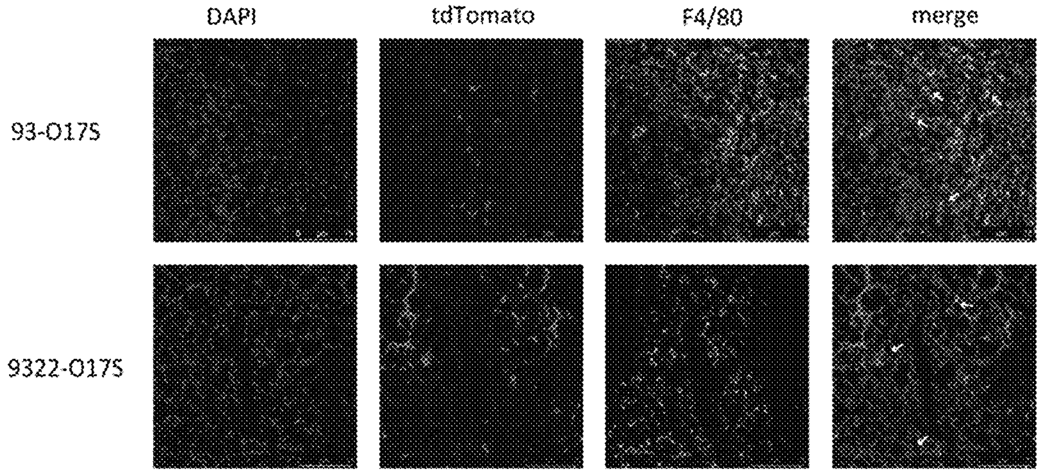
FIG. 11 shows In vivo delivery of Cre recombinase mRNA to macrophages. tdTomato expression in spleen was detected by confocal microscopy 10 days after the intravenous injection. Macrophages were labeled with F4/80 antibody.
Figure 12:
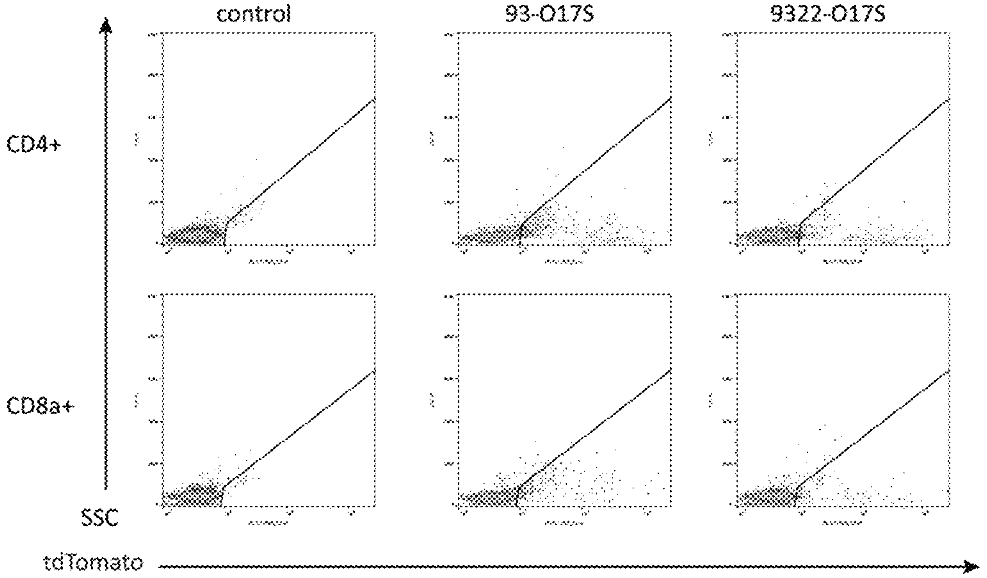
FIG. 12 are graphs that show flow cytometry dot plot of splenocytes after the in vivo delivery of Cre recombinase mRNA to Ai14 mice intravenously. 10 days after the delivery, tdTomato expression in CD4+ T cells and CD8+ T cells were analyzed.

Single cell suspension was collected from mouse spleen and tdTomato expression was quantified by the flow cytometry. Both 93-O17S and 9322-O17S showed significant expression of tdTomato signal compared to the untreated control. 93-O17S reached ~8.2% of delivery efficacy into CD4+ T cells and ~6.5% into CD8+ T cells in vivo (FIG. 10C and FIGS. 10A-10C).

INCORPORATION BY REFERENCE

All U.S. and PCT patent publications and U.S. patents mentioned herein are hereby incorporated by reference in their entirety as if each individual patent publication or patent was specifically and individually indicated to be incorporated by reference. In case of conflict, the present application, including any definitions herein, will control.

Other Embodiments

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

I claim:

1. A compound of formula I:

(I)

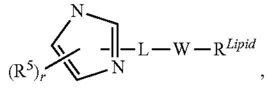

or a pharmaceutically acceptable salt thereof, wherein

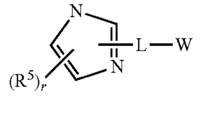

is selected from the group consisting of

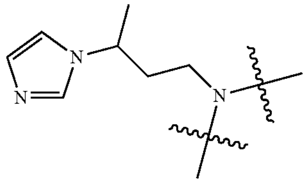

,

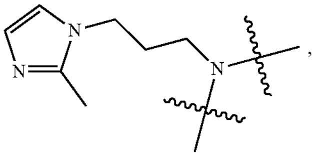

, and

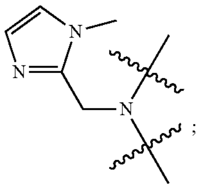

;

$R^{Lipid}$ is independently represented by a structure of formula (II):

(II)

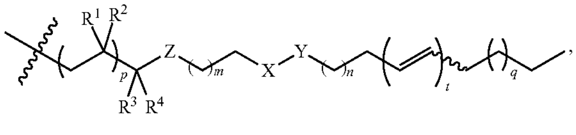

further wherein:

$R^1$ and $R^2$ are independently H, methyl, OH, $NHR^{30}$, or SH;

$R^3$ and $R^4$ are both H; or $R^3$ and $R^4$ are taken together to form an oxo (=O) group;

Z is O, $NR^{30}$, or S;

X and Y are independently $CH_2$, $NR^{30}$, O, S, or Se;

m is an integer selected from 1-3;

n is an integer selected from 1-14;

p is 0 or 1;

q is an integer selected from 1-10;

t is 0 or 1; and $R^{30}$ is H, $C_{1-6}$ alkyl, unsubstituted $C_{1-6}$ alkenyl, or unsubstituted $C_{1-6}$ alkynyl.

2. The compound of claim 1, wherein

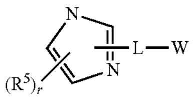

is selected from the group consisting of:

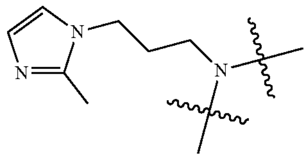

and

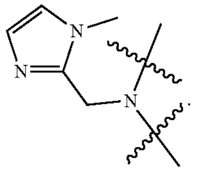

3. The compound of claim 2, wherein each instance of $R^{Lipid}$ is independently selected from the group consisting of:

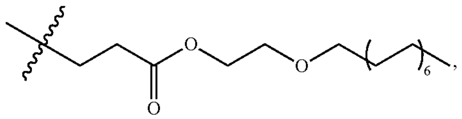

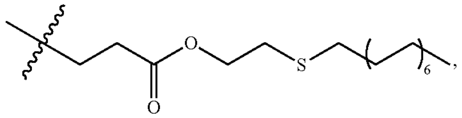

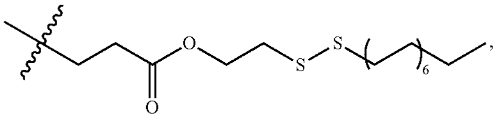

and

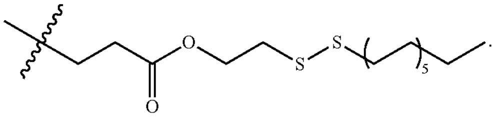

4. The compound of claim 1, wherein $R^{Lipid}$ is represented by formula II:

(II)

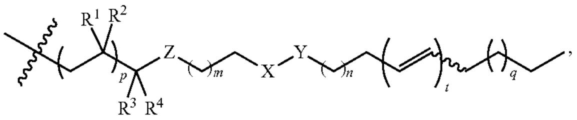

wherein $R^1$ and $R^2$ are independently H, OH, or $NHR^{30}$;

$R^3$ and $R^4$ are both H; or $R^3$ and $R^4$ are taken together to form an oxo (=O) group;

Z is O, $NR^{30}$, or S;

X and Y are independently $CH_2$, $NR^{30}$, O, S, or Se;

m is an integer selected from 1-3;

n is an integer selected from 1-14;

p is 0 or 1;

q is an integer selected from 1-10;

t is 0 or 1; and $R^{30}$ is H, unsubstituted $C_{1-6}$ alkyl, unsubstituted $C_{1-6}$ alkenyl, or unsubstituted $C_{1-6}$ alkynyl.

5. The compound of claim 1, wherein $R^1$ and $R^2$ are independently H, methyl, or OH.

6. The compound of claim 4, wherein $R^3$ and $R^4$ are both H, and at least one of $R^1$ and $R^2$ is OH.

7. The compound of claim 4, wherein $R^3$ and $R^4$ are taken together to form an oxo (=O) group.

8. The compound of claim 4, wherein Z is O or $NR^{30}$.

9. The compound of claim 1, wherein each instance of $R^{Lipid}$ is independently selected from the group consisting of

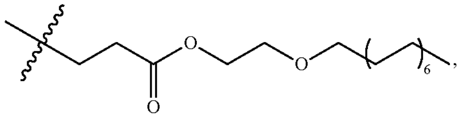

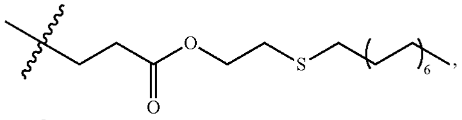

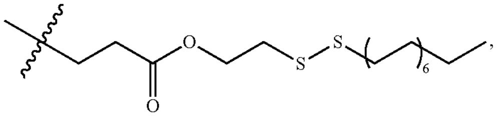

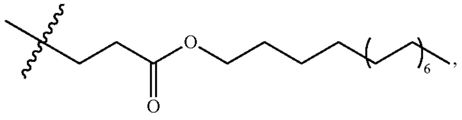

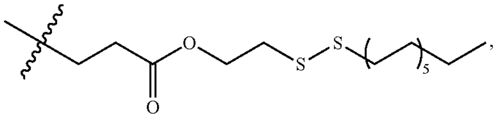

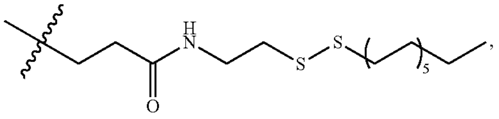

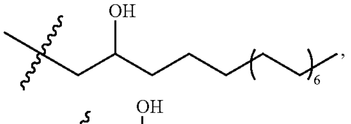

and

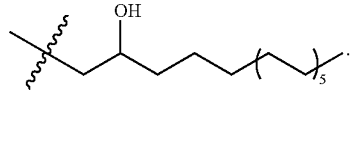

10. The compound of claim 9, wherein each instance of $R^{Lipid}$ is independently selected from the group consisting of

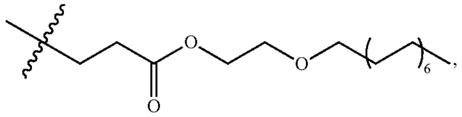

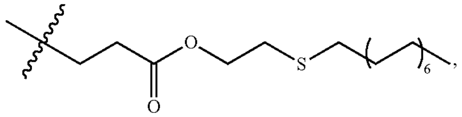

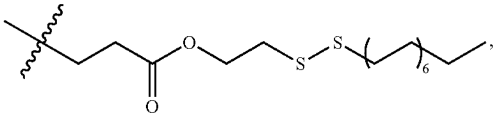

and

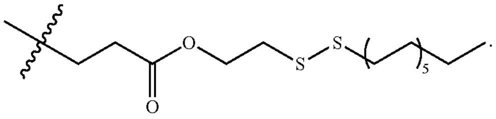

11. The compound of claim 1, wherein the compound is a compound of formula III:

(III)

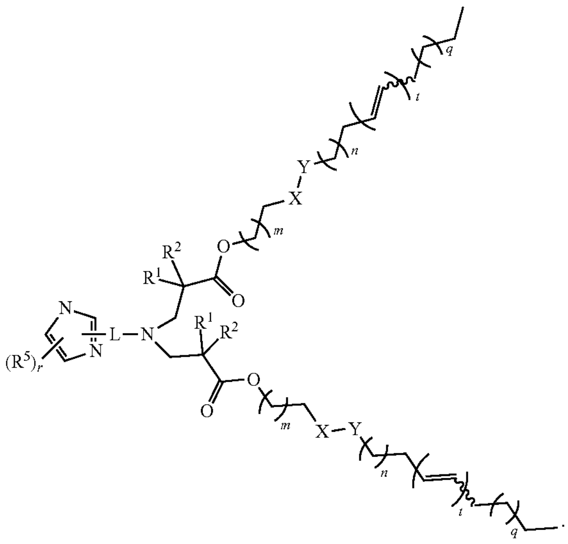

12. The compound of claim 11, wherein X and Y are independently $CH_2$, S, Se, or O.

13. The compound of claim 1, wherein

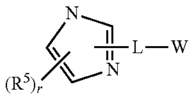

is selected from the group consisting of:

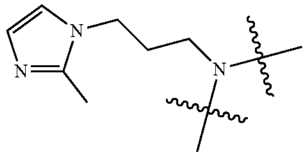

and

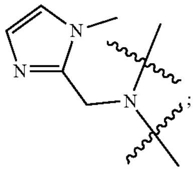

and

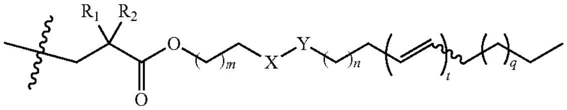

is selected from the group consisting of:

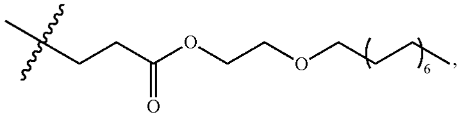

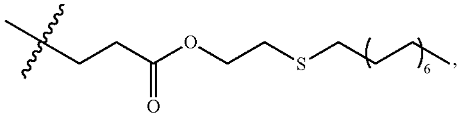

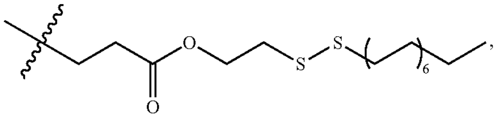

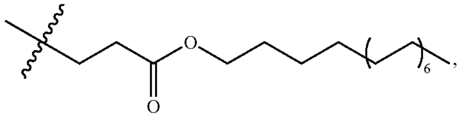

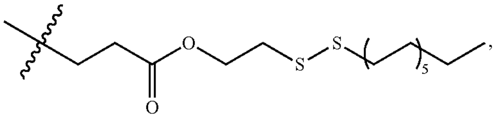

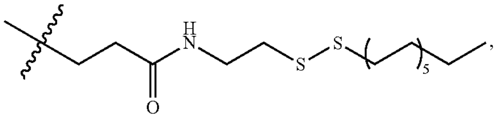

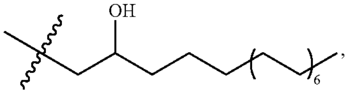

and

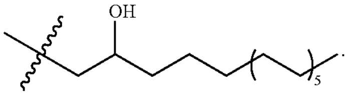

* * * * *